US010874393B2

(12) United States Patent
Satti, III et al.

(10) Patent No.: US 10,874,393 B2
(45) Date of Patent: Dec. 29, 2020

(54) PROXIMAL LOADED DISPOSABLE LOADING UNIT FOR SURGICAL STAPLER

(71) Applicant: RevMedica, Inc., Durham, CT (US)

(72) Inventors: C. Robert Satti, III, North Branford, CT (US); Thomas G. Wenchell, Jr., Durham, CT (US); Jeffrey M. Ott, New Haven, CT (US)

(73) Assignee: RevMedia, Inc., Durham, CT (US)

( * ) Notice: Subject to any disclaimer, the term of this patent is extended or adjusted under 35 U.S.C. 154(b) by 138 days.

(21) Appl. No.: 16/112,525

(22) Filed: Aug. 24, 2018

(65) Prior Publication Data
US 2019/0069895 A1    Mar. 7, 2019

Related U.S. Application Data

(60) Provisional application No. 62/616,045, filed on Jan. 11, 2018, provisional application No. 62/553,297, filed on Sep. 1, 2017.

(51) Int. Cl.
*A61B 17/072* (2006.01)
*A61B 50/30* (2016.01)
(Continued)

(52) U.S. Cl.
CPC ........ *A61B 17/07207* (2013.01); *A61B 17/00* (2013.01); *A61B 17/0682* (2013.01);
(Continued)

(58) Field of Classification Search
CPC .............. A61B 17/07207; A61B 50/30; A61B 17/1285; A61B 17/320016;
(Continued)

(56) References Cited

U.S. PATENT DOCUMENTS 3,494,799 A    2/1970 Pedone, Jr.
3,734,207 A    5/1973 Fishbein
(Continued)

FOREIGN PATENT DOCUMENTS

EP    0685203    12/1995
EP    0699418    3/1996
(Continued)

OTHER PUBLICATIONS

International search report and written opinion for international application PCT/US2018/048020 dated Oct. 30, 2018.
(Continued)

*Primary Examiner* — Robert F Long
(74) *Attorney, Agent, or Firm* — Neil D. Gershon

(57) ABSTRACT

A loading unit removably loadable into a surgical instrument positioned within a body of a patient having an elongated member, first and second jaws at a distal portion and a firing mechanism movable within the elongated member to effect firing of fasteners into the tissue clamped between the first and second jaws. The loading unit is insertable into a proximal opening of the instrument and through a lumen in the shaft of the instrument while the instrument is positioned in the body of the patient. The first and second jaws extend distally of the shaft of the instrument and the loading unit is actuable by the instrument. A surgical instrument to receive the loading unit and a method for reloading the instrument are also provided.

7 Claims, 21 Drawing Sheets

(51) Int. Cl.
  *A61B 17/128* (2006.01)
  *A61B 17/32* (2006.01)
  *A61B 17/068* (2006.01)
  *A61B 17/115* (2006.01)
  *A61B 34/30* (2016.01)
  *A61B 17/00* (2006.01)
  *A61B 17/08* (2006.01)
  *A61B 17/10* (2006.01)
  *A61B 17/29* (2006.01)
  *A61B 17/3201* (2006.01)
  *A61B 90/00* (2016.01)

(52) U.S. Cl.
  CPC .......... *A61B 17/072* (2013.01); *A61B 17/083* (2013.01); *A61B 17/10* (2013.01); *A61B 17/1155* (2013.01); *A61B 17/1285* (2013.01); *A61B 17/29* (2013.01); *A61B 17/3201* (2013.01); *A61B 17/320016* (2013.01); *A61B 34/30* (2016.02); *A61B 50/30* (2016.02); *A61B 17/00234* (2013.01); *A61B 2017/00017* (2013.01); *A61B 2017/0046* (2013.01); *A61B 2017/00115* (2013.01); *A61B 2017/00398* (2013.01); *A61B 2017/00477* (2013.01); *A61B 2017/00734* (2013.01); *A61B 2017/07257* (2013.01); *A61B 2017/07271* (2013.01); *A61B 2017/2905* (2013.01); *A61B 2017/2927* (2013.01); *A61B 2017/2929* (2013.01); *A61B 2017/2948* (2013.01); *A61B 2050/3014* (2016.02); *A61B 2090/0813* (2016.02)

(58) Field of Classification Search
  CPC . A61B 17/0682; A61B 17/1155; A61B 34/30; A61B 17/072; A61B 17/00; A61B 17/083; A61B 17/10; A61B 17/29; A61B 17/3201; A61B 2017/2927; A61B 2017/2929; A61B 2017/00017; A61B 2017/2948; A61B 2017/2905; A61B 2050/3014; A61B 2090/0813; A61B 17/00234; A61B 2017/00115; A61B 2017/00398; A61B 2017/00734; A61B 2017/07257; A61B 2017/0046; A61B 2017/07271; A61B 2017/00477
  USPC .............................................. 227/175.1–182.1
  See application file for complete search history.

(56) References Cited

U.S. PATENT DOCUMENTS

| | | |
|---|---|---|
| 4,705,038 A | 11/1987 | Sjostrom et al. |
| 4,867,158 A | 9/1989 | Sugg |
| 5,207,697 A | 5/1993 | Carusillo et al. |
| 5,261,877 A * | 11/1993 | Fine ............... A61B 17/320758 604/22 |
| 5,467,911 A * | 11/1995 | Tsuruta ............. A61B 17/0682 227/175.1 |
| 5,518,163 A | 5/1996 | Hooven |
| 5,551,622 A * | 9/1996 | Yoon ................... A61B 17/072 227/176.1 |
| 5,553,675 A | 9/1996 | Pitzen et al. |
| 5,651,491 A | 7/1997 | Heaton et al. |
| 5,680,981 A | 10/1997 | Mili et al. |
| 5,814,058 A * | 9/1998 | Carlson ............. A61B 17/3439 606/185 |
| 5,954,259 A | 9/1999 | Viola et al. |
| 6,331,181 B1 * | 12/2001 | Tierney ................. G16H 40/63 606/130 |
| 6,331,761 B1 | 12/2001 | Kumar et al. |
| 6,512,348 B1 * | 1/2003 | Wellisz ................. H02J 7/0045 320/107 |
| 6,530,931 B1 | 3/2003 | Rosenberg |
| 6,533,157 B1 | 3/2003 | Whitman |
| 6,716,233 B1 | 4/2004 | Whitman |
| 6,843,303 B2 | 1/2005 | Siak et al. |
| 6,846,307 B2 | 1/2005 | Whitman et al. |
| 6,981,141 B1 | 12/2005 | Mahne et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,461,767 B2 | 12/2008 | Viola et al. |
| 7,464,847 B2 | 12/2008 | Viola et al. |
| 7,537,602 B2 | 5/2009 | Whitman |
| 7,568,603 B2 | 8/2009 | Shelton, IV et al. |
| 7,717,312 B2 | 5/2010 | Beetel |
| 7,766,210 B2 | 8/2010 | Shelton, IV et al. |
| 7,793,812 B2 | 9/2010 | Moore et al. |
| 7,815,092 B2 | 10/2010 | Whitman et al. |
| 7,845,538 B2 | 12/2010 | Whitman |
| 7,922,063 B2 | 4/2011 | Zemlok et al. |
| 7,947,034 B2 | 5/2011 | Whitman |
| 7,950,560 B2 | 5/2011 | Zemlok et al. |
| 7,959,050 B2 | 6/2011 | Smith et al. |
| 7,963,433 B2 | 6/2011 | Whitman et al. |
| 8,006,885 B2 | 8/2011 | Marczyk |
| 8,011,551 B2 | 9/2011 | Marczyk et al. |
| 8,012,170 B2 | 9/2011 | Whitman et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,056,786 B2 | 11/2011 | Whitman et al. |
| 8,056,791 B2 | 11/2011 | Whitman |
| 8,062,311 B2 * | 11/2011 | Litscher ............. A61B 17/1285 606/143 |
| 8,074,858 B2 | 12/2011 | Marczyk |
| 8,142,473 B2 | 3/2012 | Cunningham |
| 8,157,150 B2 | 4/2012 | Viola et al. |
| 8,181,839 B2 | 5/2012 | Beetel |
| 8,186,555 B2 | 5/2012 | Shelton, IV et al. |
| 8,205,779 B2 | 6/2012 | Ma et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,899 B2 | 8/2012 | Swensgard et al. |
| 8,251,994 B2 | 8/2012 | McKenna et al. |
| 8,257,387 B2 | 9/2012 | Cunningham |
| 8,276,801 B2 | 10/2012 | Zemlok et al. |
| 8,342,377 B2 | 1/2013 | Milliman et al. |
| 8,342,378 B2 | 1/2013 | Marczyk et al. |
| 8,353,440 B2 | 1/2013 | Whitman et al. |
| 8,409,175 B2 | 4/2013 | Lee et al. |
| 8,409,222 B2 | 4/2013 | Whitfield et al. |
| 8,444,036 B2 | 5/2013 | Shelton, IV |
| 8,453,907 B2 | 6/2013 | Laurent et al. |
| 8,453,914 B2 | 6/2013 | Laurent et al. |
| 8,459,521 B2 | 6/2013 | Zemlok et al. |
| 8,459,525 B2 | 6/2013 | Yates et al. |
| 8,479,969 B2 | 7/2013 | Shelton, IV |
| 8,499,992 B2 | 8/2013 | Whitman et al. |
| 8,517,241 B2 | 8/2013 | Nicholas et al. |
| 8,551,025 B2 | 10/2013 | Soltz |
| 8,556,151 B2 | 10/2013 | Viola |
| 8,573,462 B2 | 11/2013 | Smith et al. |
| 8,573,463 B2 | 11/2013 | Scirica et al. |
| 8,602,287 B2 | 12/2013 | Yates et al. |
| 8,602,288 B2 | 12/2013 | Shelton, IV et al. |
| 8,608,045 B2 | 12/2013 | Smith et al. |
| 8,622,274 B2 | 1/2014 | Yates et al. |
| 8,631,998 B1 | 1/2014 | Viola |
| 8,636,736 B2 | 1/2014 | Yates et al. |
| 8,636,766 B2 | 1/2014 | Milliman et al. |
| 8,657,174 B2 | 2/2014 | Yates et al. |
| 8,657,177 B2 | 2/2014 | Scirica et al. |
| 8,662,371 B2 | 3/2014 | Viola |
| 8,672,206 B2 | 3/2014 | Aranyi et al. |
| 8,690,913 B2 | 4/2014 | Whitman |
| 8,708,213 B2 | 4/2014 | Shelton, IV et al. |
| 8,733,614 B2 | 5/2014 | Ross et al. |
| 8,752,748 B2 | 6/2014 | Whitman et al. |
| 8,764,749 B2 | 7/2014 | Mckenna et al. |

(56) References Cited

U.S. PATENT DOCUMENTS

| | | |
|---|---|---|
| 8,777,945 B2 | 7/2014 | Floume et al. |
| 8,795,313 B2 | 8/2014 | Liang et al. |
| 8,800,837 B2 | 8/2014 | Zemlok |
| 8,820,603 B2 | 9/2014 | Shelton, IV et al. |
| 8,821,514 B2 | 9/2014 | Aranyi |
| 8,827,134 B2 | 9/2014 | Viola et al. |
| 8,834,466 B2 | 9/2014 | Cummings et al. |
| 8,851,355 B2 | 10/2014 | Aranyi et al. |
| 8,864,753 B2 | 10/2014 | Nau, Jr. et al. |
| 8,875,973 B2 | 11/2014 | Whitman |
| 8,899,462 B2 | 12/2014 | Kostrzewski et al. |
| 8,911,471 B2 | 12/2014 | Spivey et al. |
| 8,955,732 B2 | 2/2015 | Zemlok et al. |
| 8,960,520 B2 | 2/2015 | McCuen |
| 8,967,443 B2 | 3/2015 | McCuen |
| 8,968,276 B2 | 3/2015 | Zemlok et al. |
| 8,968,285 B2 | 3/2015 | Twomey et al. |
| 8,991,677 B2 | 3/2015 | Moore et al. |
| 8,998,058 B2 | 4/2015 | Moore et al. |
| 9,017,355 B2 | 4/2015 | Smith et al. |
| 9,028,478 B2 | 5/2015 | Mueller |
| 9,072,523 B2 | 7/2015 | Houser et al. |
| 9,084,601 B2 | 7/2015 | Moore et al. |
| 9,095,339 B2 | 8/2015 | Moore et al. |
| 9,101,358 B2 | 8/2015 | Kerr et al. |
| 9,113,874 B2 | 8/2015 | Shelton, IV et al. |
| 9,113,880 B2 | 8/2015 | Zemlok et al. |
| 9,113,901 B2 | 8/2015 | Allen, IV et al. |
| 9,186,143 B2 | 11/2015 | Timm et al. |
| 9,192,381 B2 | 11/2015 | Marczyk |
| 9,241,716 B2 | 1/2016 | Whitman |
| 9,265,585 B2 | 2/2016 | Wingardner et al. |
| 9,301,772 B2 | 4/2016 | Kimball et al. |
| 9,320,520 B2 | 4/2016 | Shelton, IV et al. |
| 9,326,770 B2 | 5/2016 | Shelton, IV et al. |
| 9,326,812 B2 | 5/2016 | Waaler et al. |
| 9,351,727 B2 | 5/2016 | Leimbach et al. |
| 9,364,220 B2 | 6/2016 | Williams |
| 9,364,224 B2 | 6/2016 | Nicholas et al. |
| 9,370,364 B2 | 6/2016 | Smith et al. |
| 9,393,015 B2 | 7/2016 | Laurent et al. |
| 9,398,911 B2 | 7/2016 | Auld |
| 9,402,604 B2 | 8/2016 | Williams et al. |
| 9,414,818 B2 * | 8/2016 | Azarbarzin ............ A61B 17/29 |
| 9,421,003 B2 | 8/2016 | Williams et al. |
| 9,421,014 B2 | 8/2016 | Ingmanson et al. |
| 9,433,415 B2 | 9/2016 | Marczyk et al. |
| 9,451,958 B2 | 9/2016 | Shelton, IV et al. |
| 9,468,454 B2 | 10/2016 | Johnson et al. |
| 9,474,528 B2 | 10/2016 | Marczyk |
| 9,484,657 B2 | 11/2016 | Martin et al. |
| 9,486,214 B2 | 11/2016 | Shelton, IV |
| 9,492,167 B2 | 11/2016 | Shelton, IV et al. |
| 9,504,520 B2 | 11/2016 | Worell et al. |
| 9,517,068 B2 | 12/2016 | Shelton, IV et al. |
| 9,539,006 B2 | 1/2017 | Collings et al. |
| 9,549,750 B2 | 1/2017 | Shelton, IV et al. |
| 9,554,803 B2 | 1/2017 | Smith et al. |
| 9,561,031 B2 | 2/2017 | Heinrich et al. |
| 9,585,672 B2 * | 3/2017 | Bastia ............ A61B 17/00234 |
| 9,592,056 B2 | 3/2017 | Mozdzierz et al. |
| 9,597,081 B2 | 3/2017 | Swayze et al. |
| 9,615,828 B2 | 4/2017 | Scirica |
| 9,622,744 B2 | 4/2017 | Smith et al. |
| 9,636,091 B2 | 5/2017 | Beardsley et al. |
| 9,649,110 B2 | 5/2017 | Parihar et al. |
| 9,655,614 B2 | 5/2017 | Swensgard et al. |
| 9,662,110 B2 | 5/2017 | Huang et al. |
| 9,675,348 B2 | 6/2017 | Smith et al. |
| 9,685,281 B2 | 6/2017 | Wang et al. |
| 9,687,230 B2 | 6/2017 | Leimbach et al. |
| 9,687,234 B2 | 6/2017 | Smith et al. |
| 9,687,236 B2 | 6/2017 | Leimbach et al. |
| 9,687,253 B2 | 6/2017 | Detry et al. |
| 9,700,310 B2 | 7/2017 | Moragan et al. |
| 9,700,318 B2 | 7/2017 | Scirica et al. |
| 9,743,928 B2 | 8/2017 | Shelton, IV et al. |
| 9,750,499 B2 | 9/2017 | Leimbach et al. |
| 9,775,610 B2 | 10/2017 | Nicholas et al. |
| 9,782,172 B2 | 10/2017 | Whitman |
| 9,782,187 B2 | 10/2017 | Zergiebal et al. |
| 9,788,836 B2 | 10/2017 | Overmyer et al. |
| 9,797,486 B2 | 10/2017 | Zergiebel et al. |
| 9,801,626 B2 | 10/2017 | Parilhar et al. |
| 9,826,976 B2 | 11/2017 | Parihar et al. |
| 9,833,235 B2 | 12/2017 | Penna et al. |
| 9,844,368 B2 | 12/2017 | Boudreanx et al. |
| 9,844,375 B2 | 12/2017 | Overmyer et al. |
| 9,867,612 B2 | 1/2018 | Parilhar et al. |
| 9,877,720 B2 | 1/2018 | Worrell et al. |
| 9,901,344 B2 | 2/2018 | Moore et al. |
| 9,901,346 B2 | 2/2018 | Moore et al. |
| 9,907,552 B2 | 3/2018 | Measamer et al. |
| 9,924,942 B2 | 3/2018 | Swayze et al. |
| 9,936,949 B2 | 4/2018 | Measamer et al. |
| 9,936,951 B2 | 4/2018 | Hufnagel et al. |
| 9,937,626 B2 | 4/2018 | Rockrohr |
| 9,949,737 B2 | 4/2018 | Zergiebel et al. |
| 9,955,965 B2 | 5/2018 | Chen et al. |
| 9,955,966 B2 | 5/2018 | Zergiebel |
| 9,962,157 B2 | 5/2018 | Sapre |
| 9,962,159 B2 | 5/2018 | Heunrich et al. |
| 9,974,539 B2 | 5/2018 | Yates et al. |
| 9,980,729 B2 | 5/2018 | Moore et al. |
| 9,991,069 B2 | 6/2018 | Nicholas et al. |
| 10,004,498 B2 | 6/2018 | Morgan et al. |
| 10,041,822 B2 | 8/2018 | Zemlok |
| 10,052,100 B2 | 8/2018 | Morgan et al. |
| 10,064,621 B2 | 9/2018 | Kerr et al. |
| 10,070,861 B2 | 9/2018 | Spivey et al. |
| 10,076,379 B2 | 9/2018 | Boudreaux |
| 10,085,752 B2 | 10/2018 | Williams et al. |
| 10,111,662 B2 | 10/2018 | Zemlok et al. |
| 10,111,665 B2 | 10/2018 | Aranyi et al. |
| 10,117,654 B2 | 11/2018 | Ingmanson et al. |
| 10,136,887 B2 | 11/2018 | Shelton, IV et al. |
| 10,143,472 B2 | 12/2018 | Williams |
| 10,149,683 B2 | 12/2018 | Smith et al. |
| 10,172,612 B2 | 1/2019 | Frushour |
| 10,178,992 B2 | 1/2019 | Wise et al. |
| 10,180,463 B2 | 1/2019 | Beckman et al. |
| 10,190,888 B2 | 1/2019 | Hryb et al. |
| 10,194,907 B2 | 2/2019 | Marczyk et al. |
| 10,220,522 B2 | 3/2019 | Rockrohr |
| 10,226,249 B2 | 3/2019 | Jaworek et al. |
| 10,226,250 B2 | 3/2019 | Beckman et al. |
| 10,245,033 B2 | 4/2019 | Overmyer et al. |
| 10,568,651 B2 | 2/2020 | Kostrzewski |
| 2002/0143346 A1 * | 10/2002 | McGuckin, Jr. ........................... A61B 17/07207 606/139 |
| 2005/0107809 A1 * | 5/2005 | Litscher ............ A61B 17/1285 606/142 |
| 2005/0187576 A1 * | 8/2005 | Whitman ............ A61B 17/068 606/219 |
| 2007/0023477 A1 | 2/2007 | Whitman |
| 2007/0118163 A1 * | 5/2007 | Boudreaux ........ A61B 17/1227 606/157 |
| 2008/0203135 A1 | 8/2008 | Viola et al. |
| 2008/0255597 A1 * | 10/2008 | Pravong ........... A61B 17/32002 606/169 |
| 2008/0281353 A1 | 11/2008 | Aranyi et al. |
| 2008/0296346 A1 | 12/2008 | Shelton, IV |
| 2009/0095790 A1 | 4/2009 | Whitman |
| 2009/0110533 A1 | 4/2009 | Jinno |
| 2009/0171243 A1 | 7/2009 | Hibner |
| 2009/0182193 A1 | 7/2009 | Whitman |
| 2009/0312603 A1 * | 12/2009 | Lam ........ A61B 1/018 600/106 |
| 2010/0320252 A1 * | 12/2010 | Viola ............ A61B 17/07207 227/176.1 |
| 2011/0011915 A1 | 1/2011 | Shelton, IV |

(56) References Cited

U.S. PATENT DOCUMENTS

| | | | |
|---|---|---|---|
| 2011/0022032 A1* | 1/2011 | Zemlok | A61B 17/07207 606/1 |
| 2011/0082471 A1* | 4/2011 | Holcomb | A61B 17/0401 606/139 |
| 2011/0125176 A1 | 5/2011 | Yates et al. | |
| 2011/0282381 A1* | 11/2011 | Cronin | A61B 10/0275 606/213 |
| 2012/0061446 A1* | 3/2012 | Knodel | A61B 17/07207 227/175.1 |
| 2012/0172924 A1 | 7/2012 | Allen, IV | |
| 2012/0199632 A1* | 8/2012 | Spivey | A61B 34/30 227/176.1 |
| 2012/0286021 A1 | 11/2012 | Kostrzewski | |
| 2012/0298719 A1* | 11/2012 | Shelton, IV | A61B 17/105 227/176.1 |
| 2013/0098968 A1 | 4/2013 | Aranyi | |
| 2013/0181033 A1 | 7/2013 | Shelton, IV et al. | |
| 2013/0331847 A1* | 12/2013 | Smith | A61B 17/8816 606/94 |
| 2014/0005718 A1 | 1/2014 | Shelton, IV et al. | |
| 2014/0175150 A1 | 6/2014 | Shelton, IV | |
| 2014/0213848 A1* | 7/2014 | Moskowitz | A61B 1/00133 600/106 |
| 2014/0246471 A1 | 9/2014 | Jaworek | |
| 2014/0257252 A1* | 9/2014 | Ishida | A61B 17/00234 606/1 |
| 2014/0277334 A1 | 9/2014 | Yu | |
| 2014/0291383 A1* | 10/2014 | Spivey | A61B 34/30 227/177.1 |
| 2014/0305987 A1 | 10/2014 | Parihar | |
| 2014/0305995 A1 | 10/2014 | Shelton, IV et al. | |
| 2014/0309666 A1 | 10/2014 | Shelton, IV | |
| 2015/0053737 A1 | 2/2015 | Leimbach | |
| 2015/0090760 A1 | 4/2015 | Giordano et al. | |
| 2015/0126977 A1* | 5/2015 | Azarbarzin | A61B 17/29 606/1 |
| 2015/0150547 A1 | 6/2015 | Ingmanson | |
| 2016/0058443 A1 | 3/2016 | Yates et al. | |
| 2016/0095585 A1 | 4/2016 | Zergiebel et al. | |
| 2016/0213436 A1* | 7/2016 | Inoue | A61B 17/3421 |
| 2016/0220247 A1 | 8/2016 | Timm et al. | |
| 2016/0249922 A1 | 9/2016 | Morgan et al. | |
| 2016/0270780 A1 | 9/2016 | Hall | |
| 2016/0310134 A1 | 10/2016 | Contini et al. | |
| 2017/0007254 A1 | 1/2017 | Jaworek | |
| 2017/0007255 A1 | 1/2017 | Jaworek et al. | |
| 2017/0035421 A1 | 2/2017 | Marczyk | |
| 2017/0079640 A1 | 3/2017 | Overmyer et al. | |
| 2017/0079642 A1 | 3/2017 | Overmyer et al. | |
| 2017/0128071 A1* | 5/2017 | Holsten | A61B 17/105 |
| 2017/0164945 A1 | 6/2017 | Chowaniec | |
| 2017/0172574 A1 | 6/2017 | Zemlok et al. | |
| 2017/0189020 A1 | 7/2017 | Harris et al. | |
| 2017/0290583 A1 | 10/2017 | Reed et al. | |
| 2017/0296176 A1 | 10/2017 | Contini et al. | |
| 2018/0000483 A1 | 1/2018 | Leimbach et al. | |
| 2018/0056496 A1* | 3/2018 | Rubens | B44B 7/02 |
| 2018/0133883 A1 | 5/2018 | Nicholas et al. | |
| 2018/0317964 A1 | 11/2018 | Evans et al. | |
| 2018/0360486 A1* | 12/2018 | Beaupre | A61B 17/32 |
| 2018/0368822 A1 | 12/2018 | Shelon et al. | |
| 2019/0000577 A1* | 1/2019 | Shelton, IV | A61B 34/37 |
| 2019/0008512 A1 | 1/2019 | Nicholas et al. | |
| 2019/0053796 A1 | 2/2019 | Miller et al. | |
| 2019/0059923 A1* | 2/2019 | Tillman | A61B 18/1445 |
| 2019/0069887 A1 | 3/2019 | Satti, III et al. | |
| 2019/0069895 A1 | 3/2019 | Satti, III et al. | |
| 2019/0069896 A1* | 3/2019 | Satti, III | A61B 17/1285 |
| 2019/0142421 A1* | 5/2019 | Shelton, IV | A61M 39/1055 606/130 |
| 2019/0142423 A1* | 5/2019 | Satti, III | A61B 17/072 227/176.1 |
| 2019/0261991 A1 | 8/2019 | Beckman | |

FOREIGN PATENT DOCUMENTS

| | | |
|---|---|---|
| EP | 0705571 | 4/1996 |
| EP | 1889576 | 2/2008 |
| EP | 2243432 | 10/2010 |
| EP | 2243433 | 10/2010 |
| EP | 3005954 | 4/2016 |
| EP | 3078334 | 10/2016 |
| EP | 3178413 | 6/2017 |
| EP | 3189790 | 7/2017 |
| EP | 2792316 | 1/2018 |
| WO | WO 2010/006057 | 1/2010 |

OTHER PUBLICATIONS

International search report for international application PCT/US2018/046370 dated Nov. 6, 2018.

\* cited by examiner

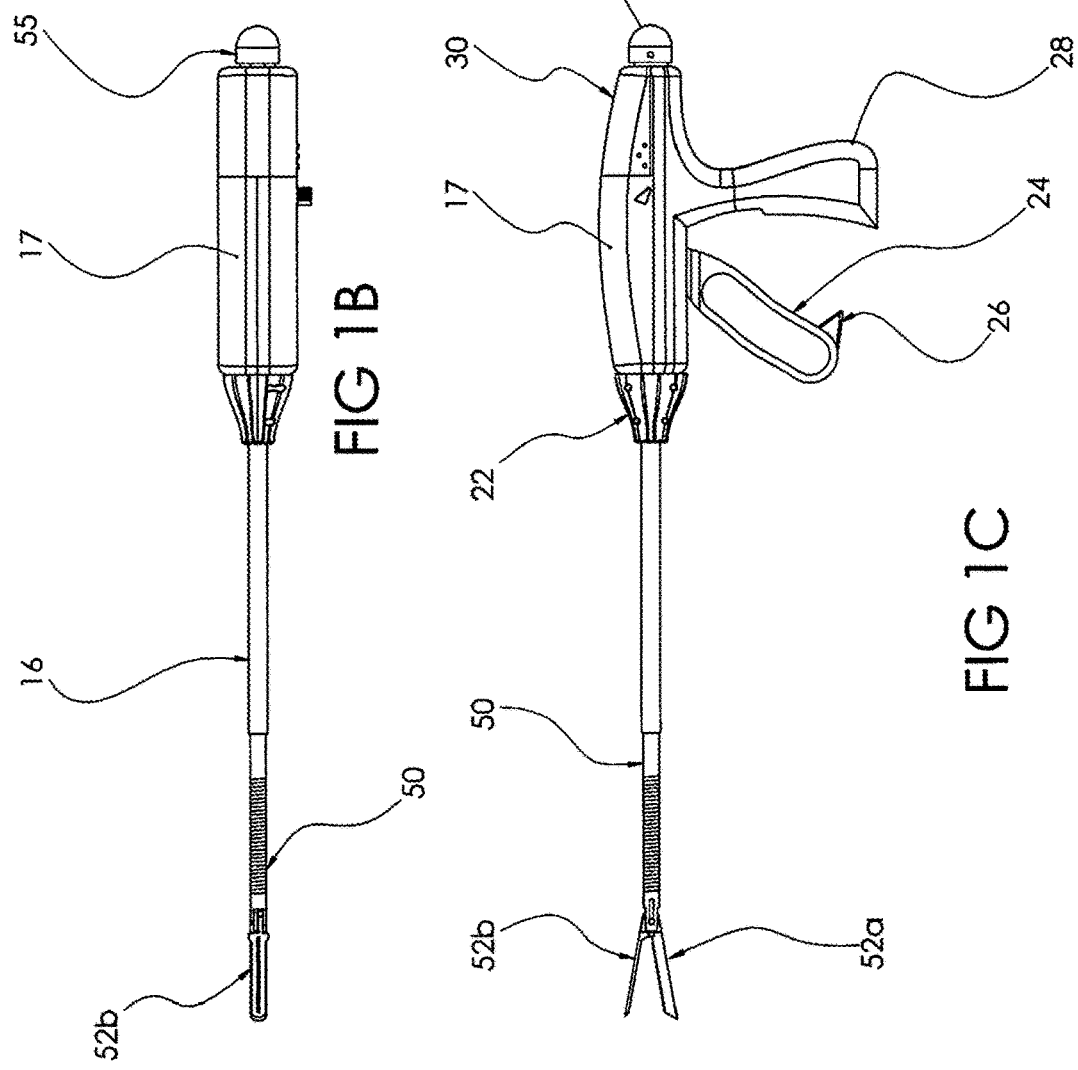

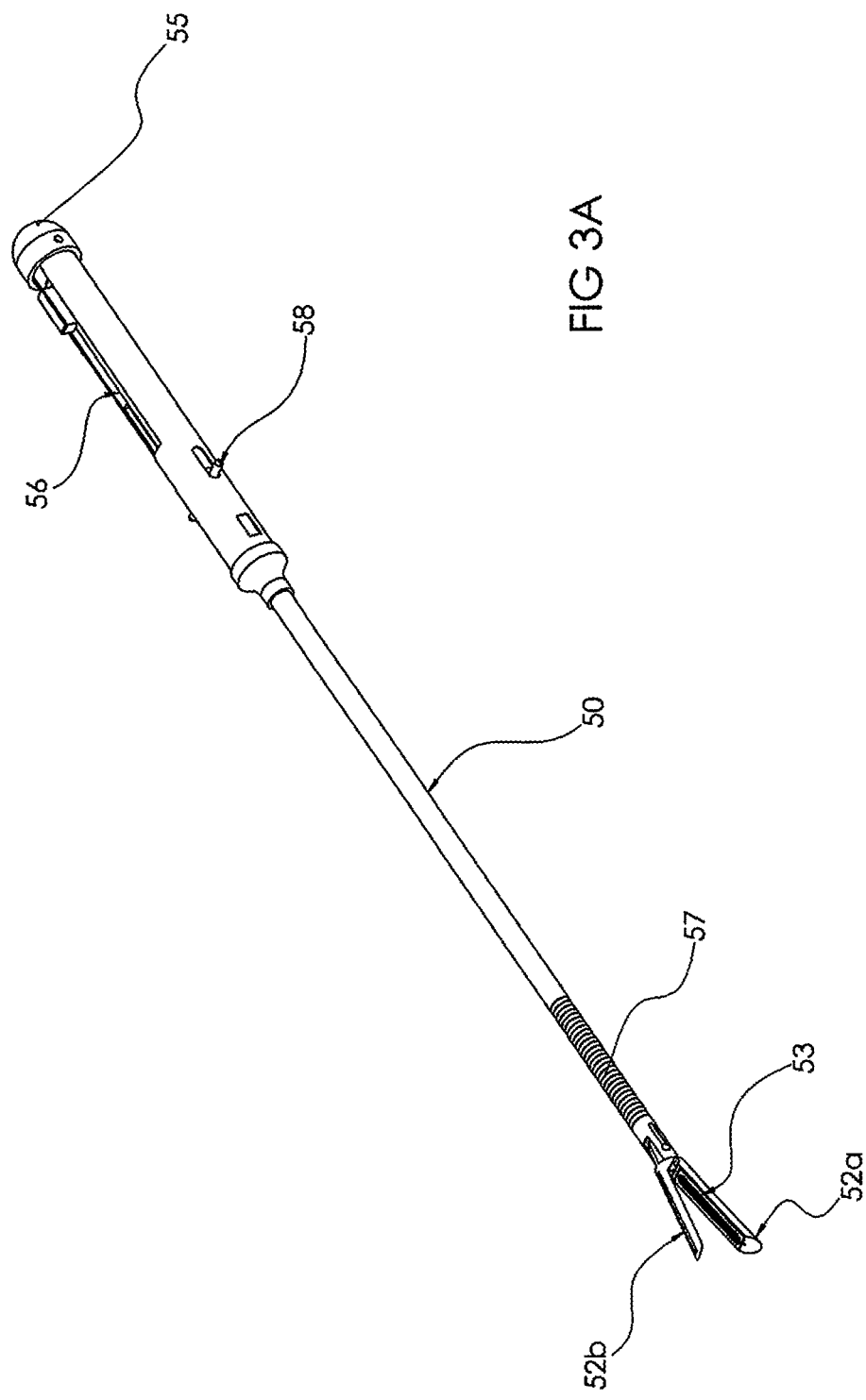

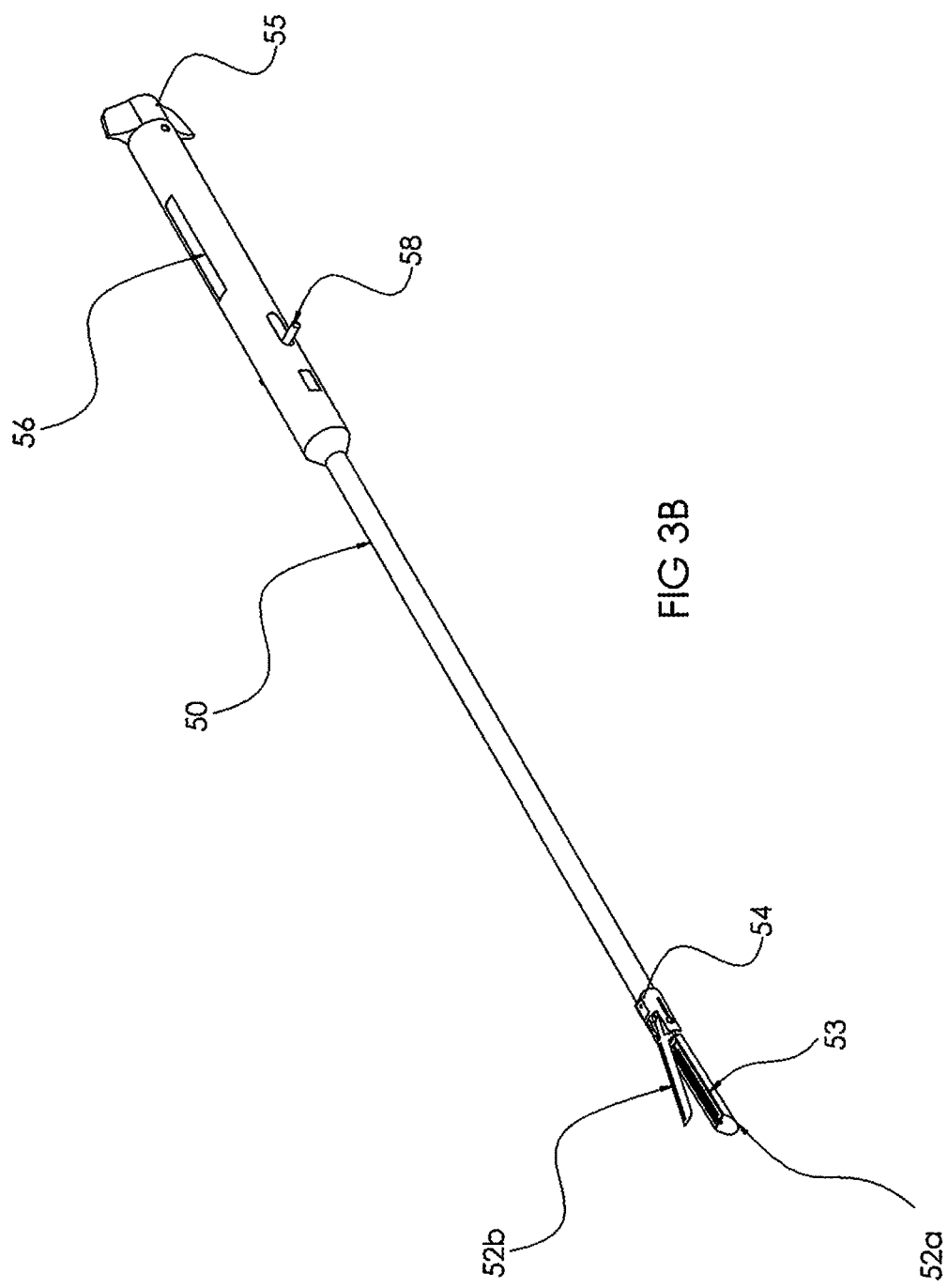

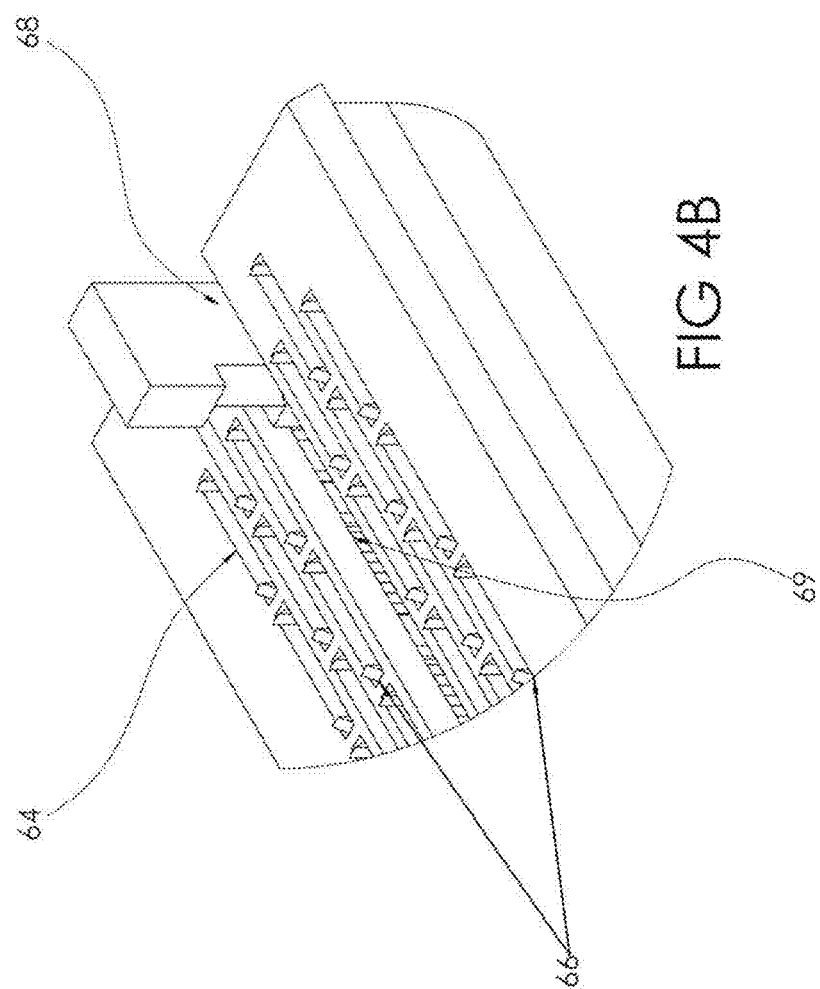
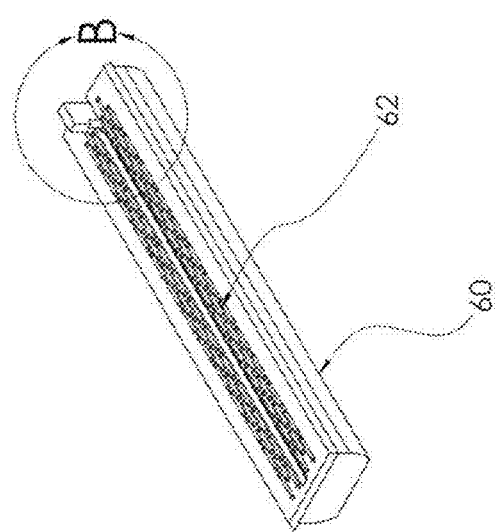
FIG 4B
FIG 4A

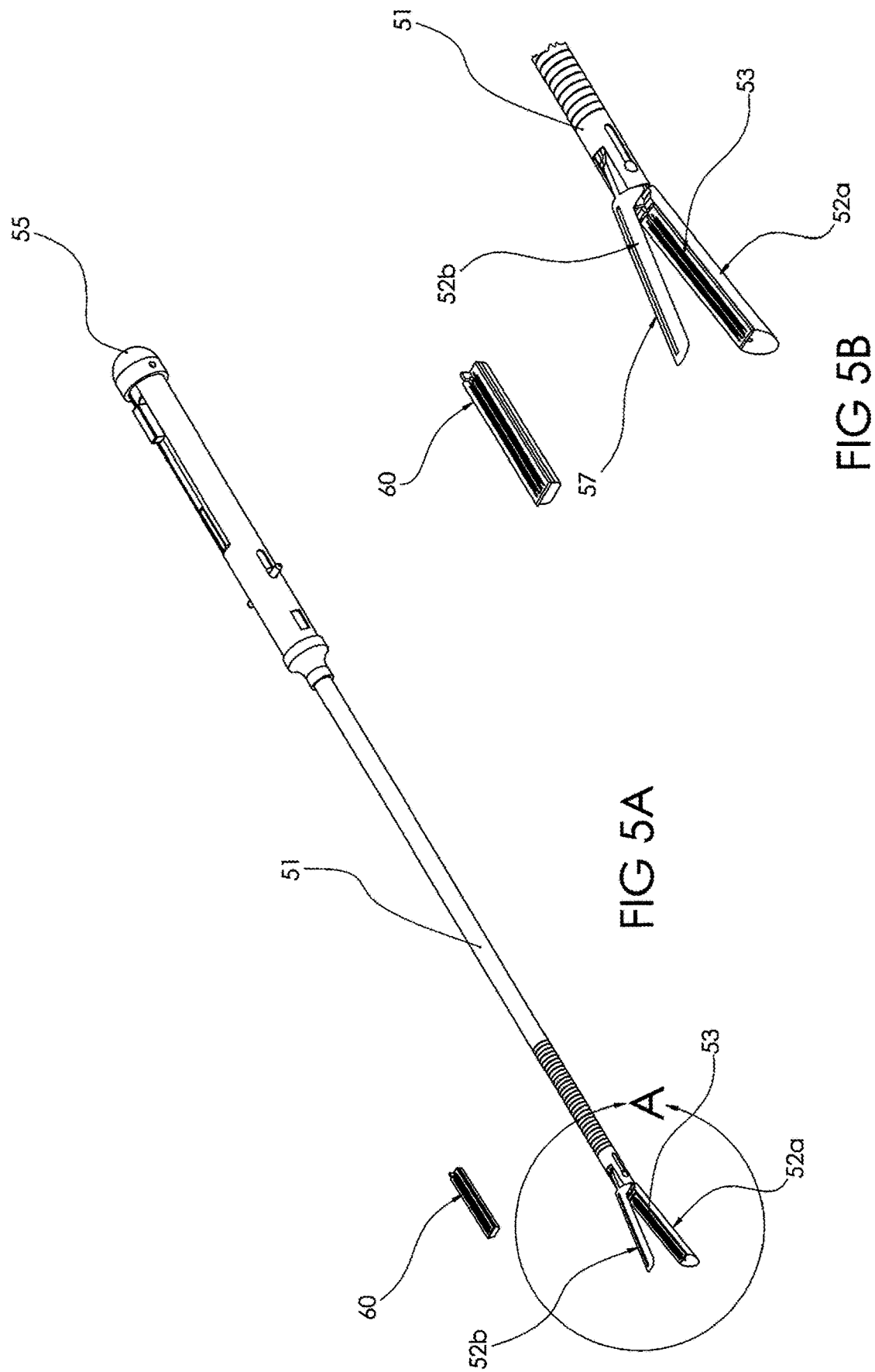

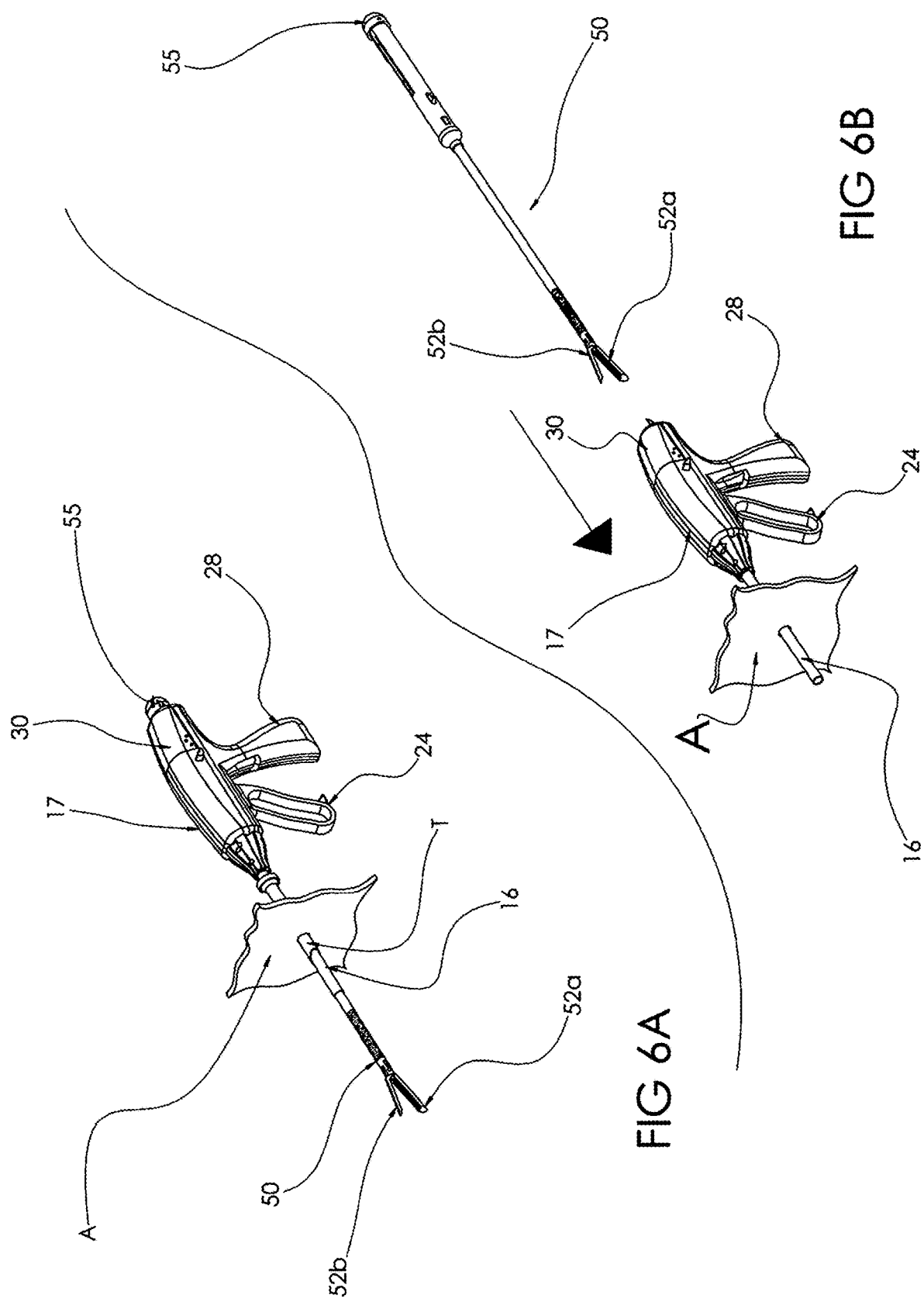

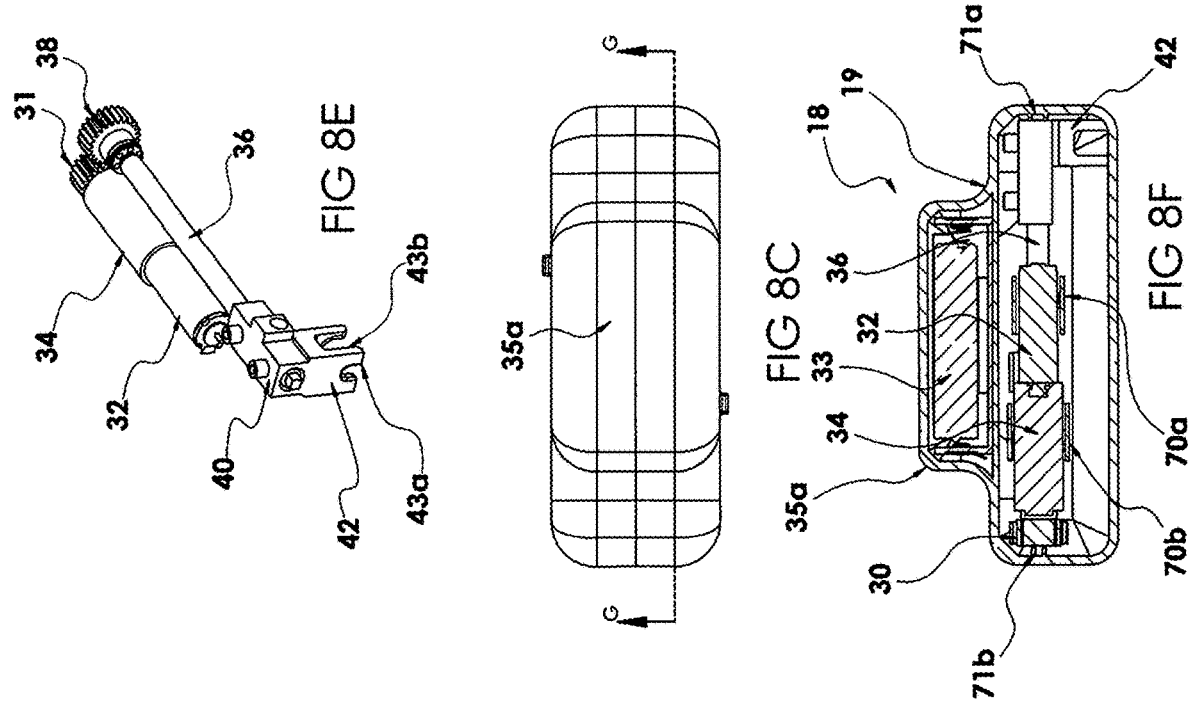
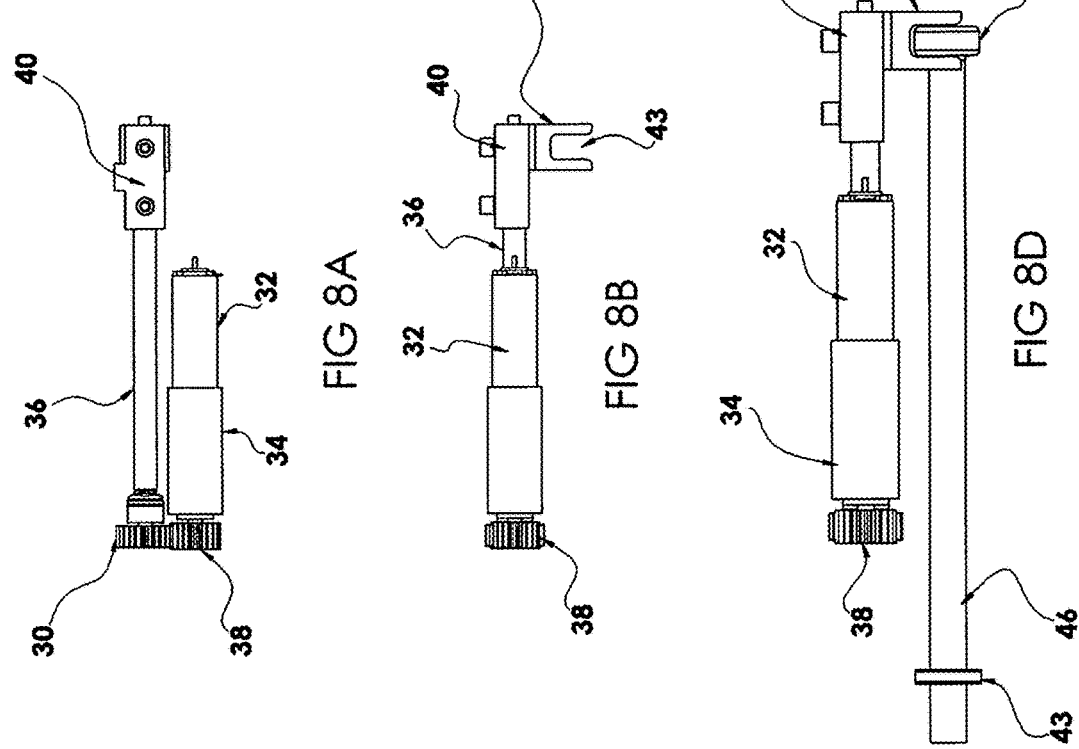

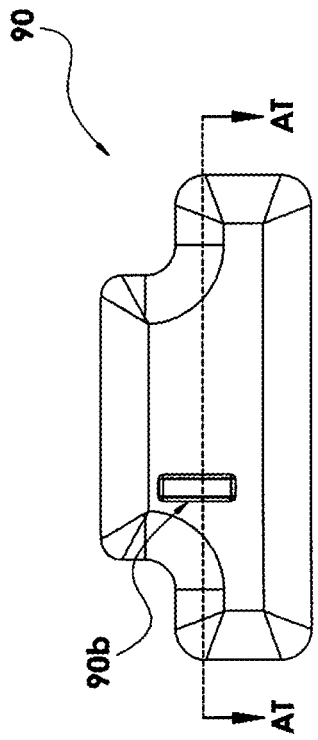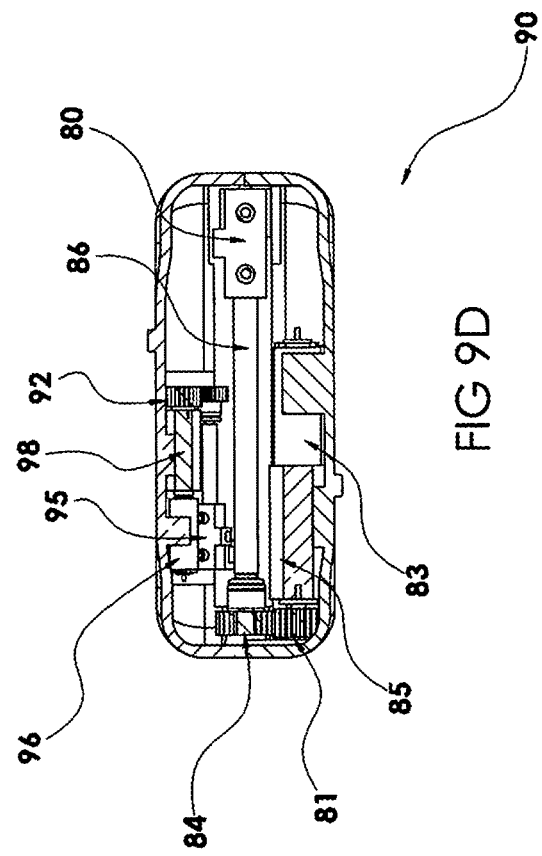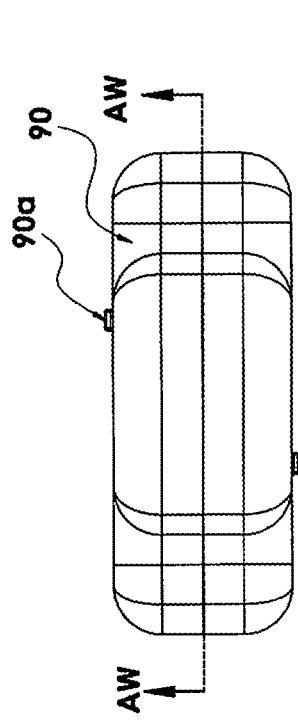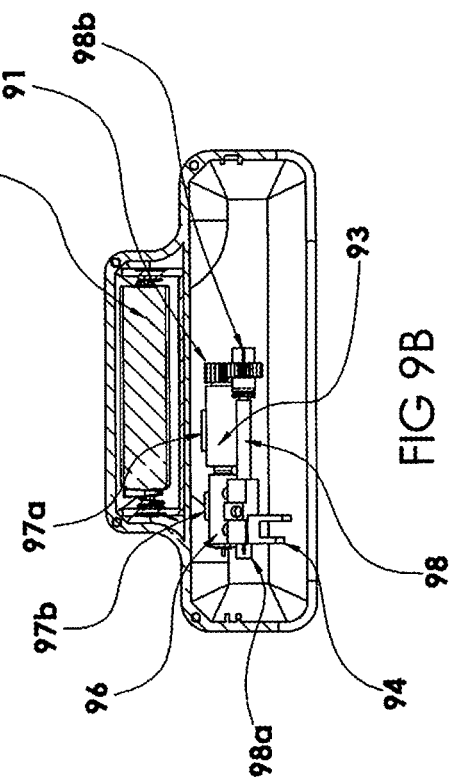

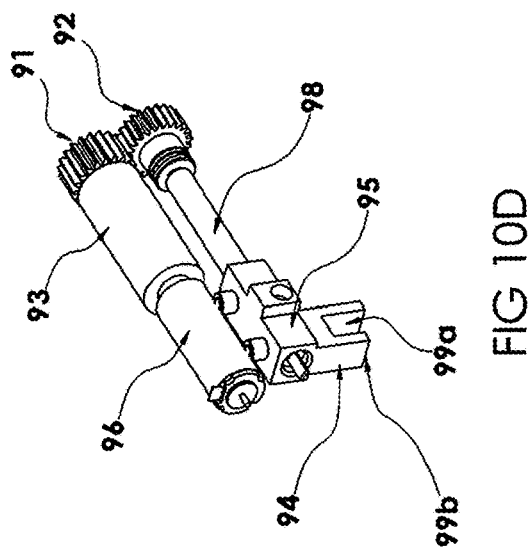
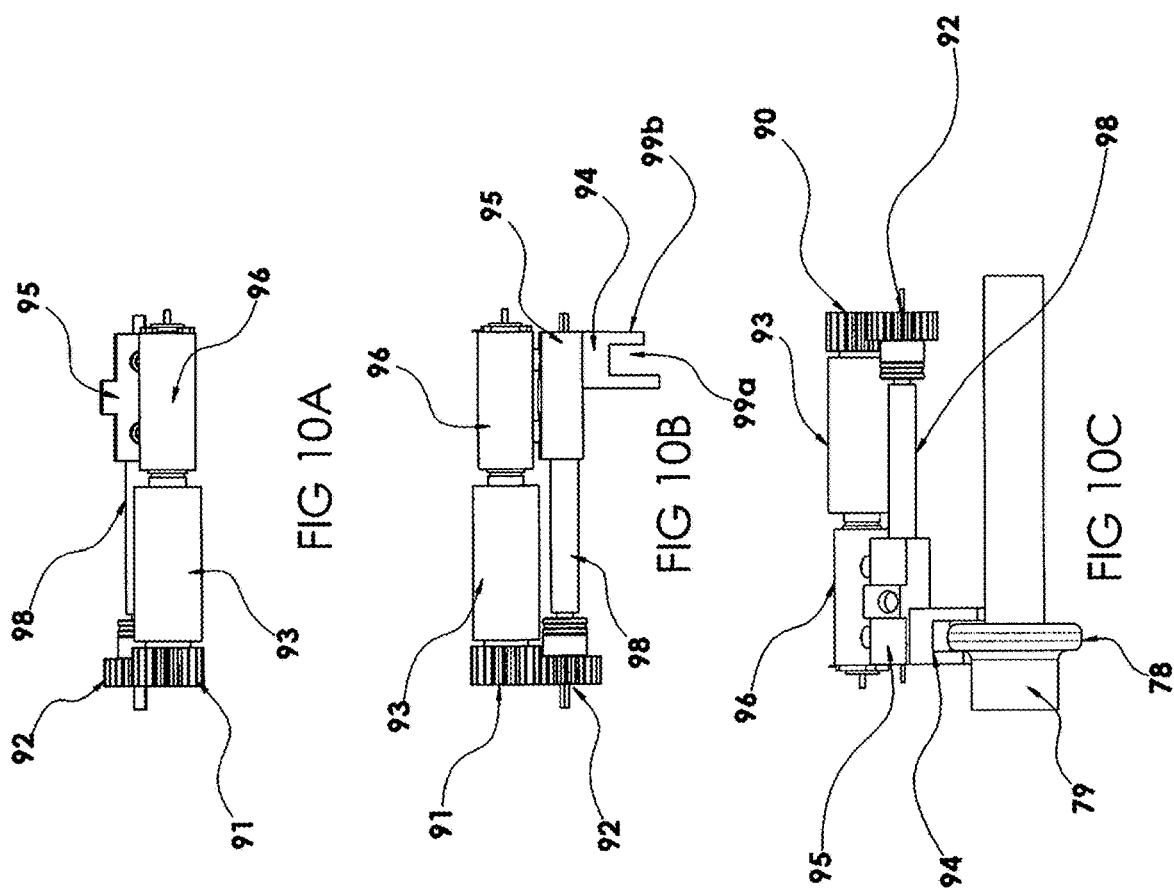

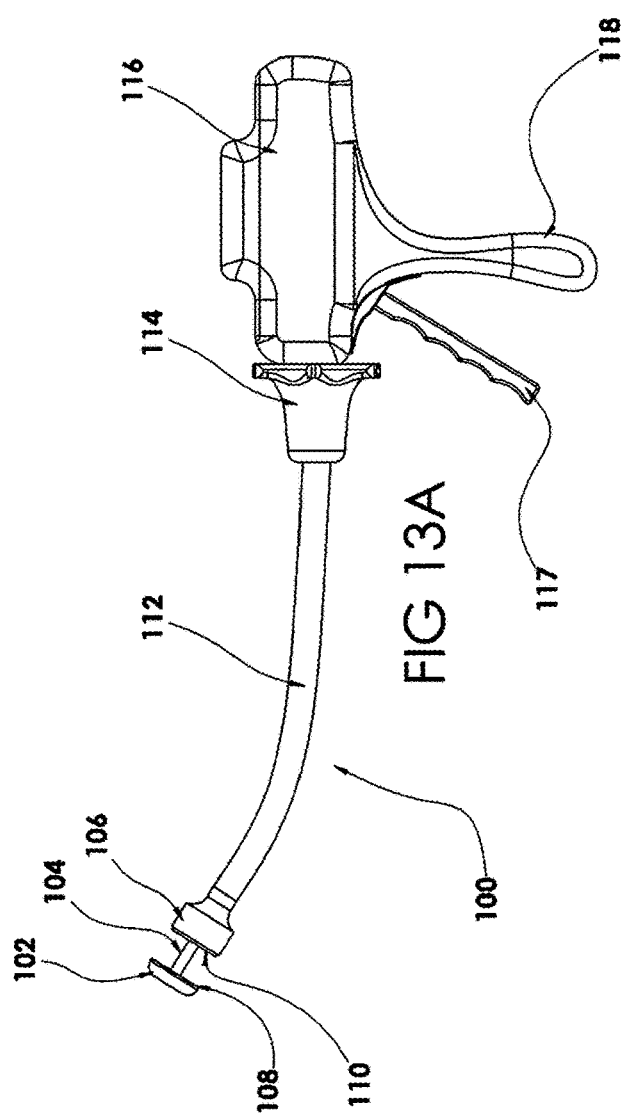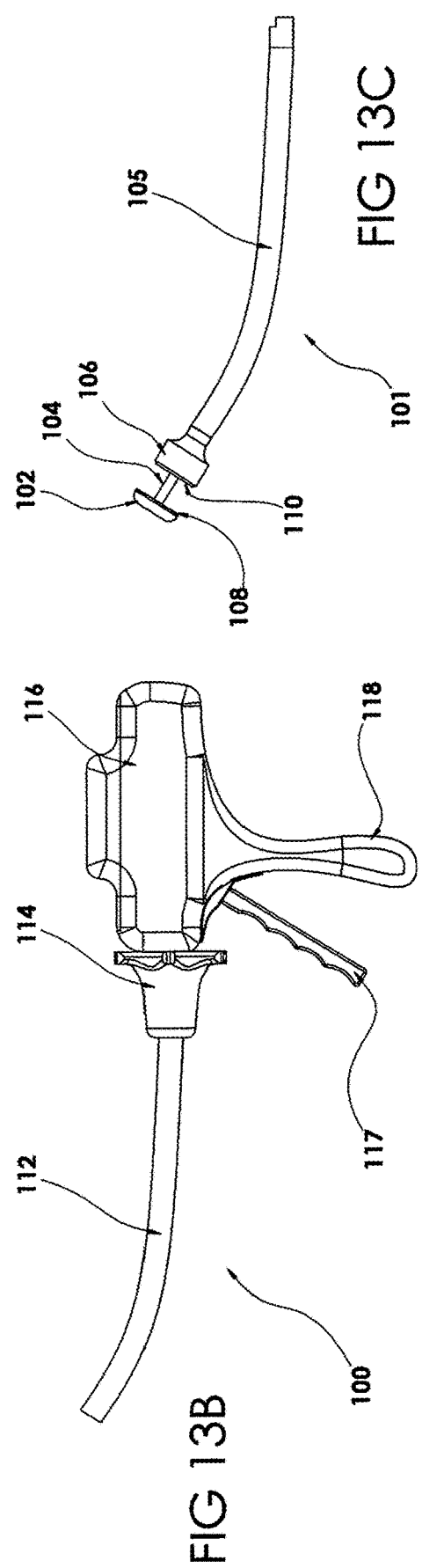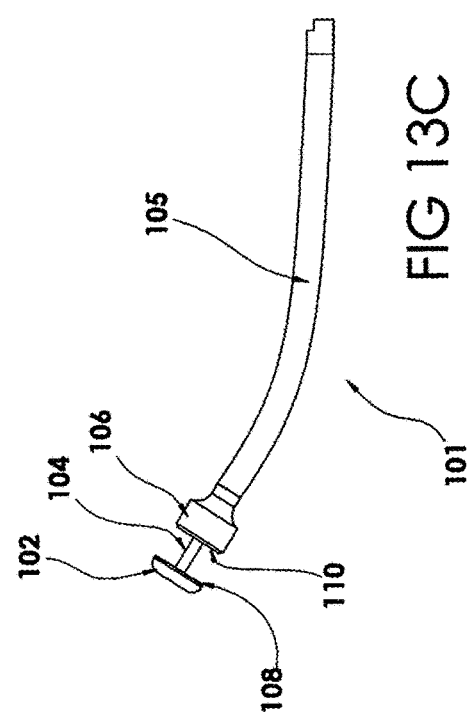

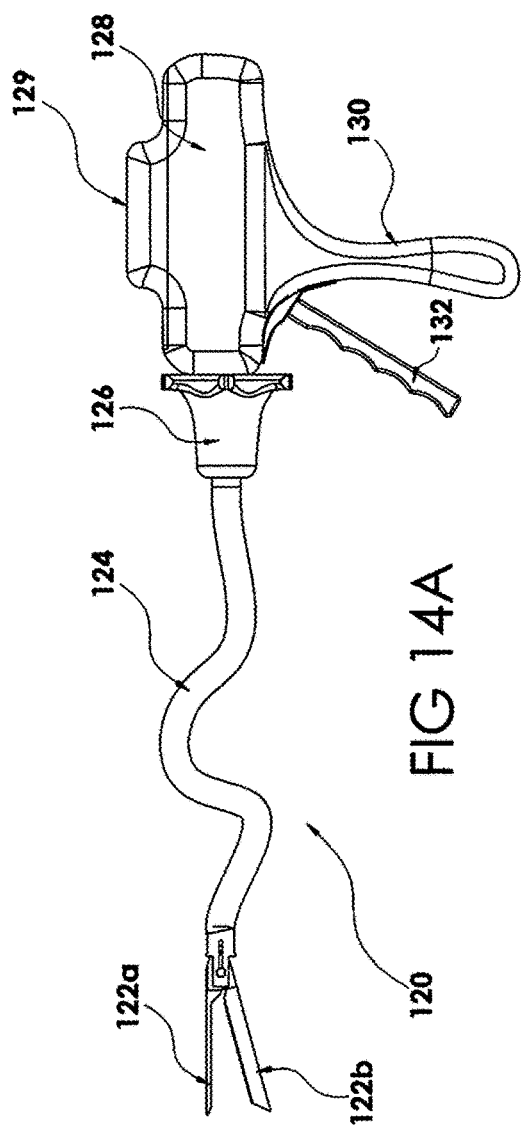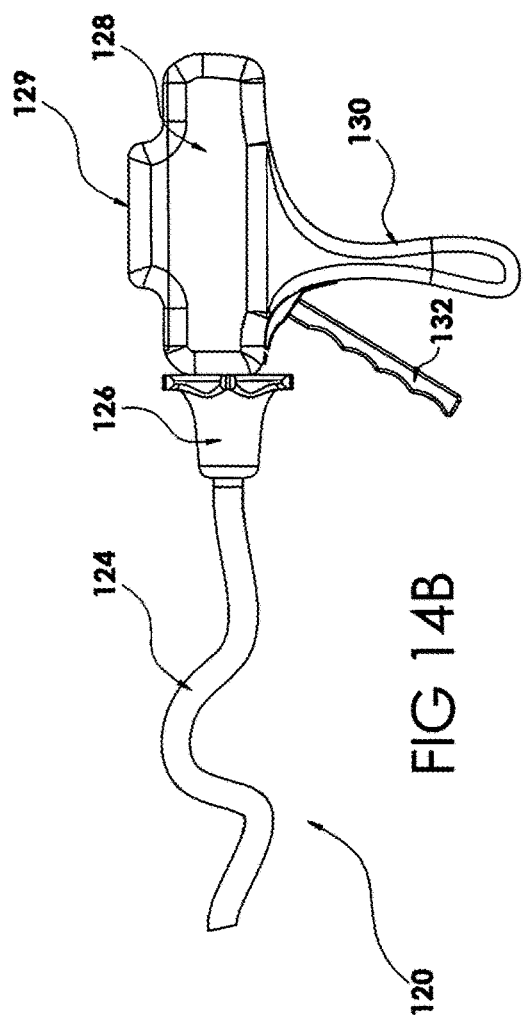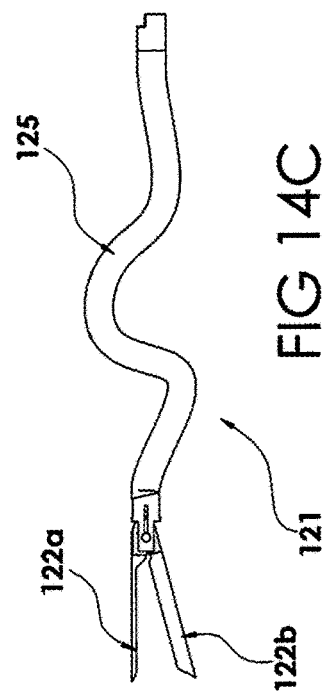

PROXIMAL LOADED DISPOSABLE LOADING UNIT FOR SURGICAL STAPLER

This application claims priority from provisional application Ser. No. 62/553,297 filed Sep. 1, 2017, and from provisional application Ser. No. 62/616,045, filed Jan. 11, 2018. The entire contents of each of these applications are incorporated herein by reference.

BACKGROUND OF THE INVENTION

1. Field of the Invention

This application relates to surgical staplers, and more particularly, to loading units for surgical staplers.

2. Background

Surgical staplers are used in various medical applications where a device is needed to simultaneously join and dissect anatomical tissue. The staplers are generally used in either open or minimally invasive, e.g., laparoscopic, surgical procedures. Surgical staplers typically require the user to actuate the device, dissecting and joining a given length of anatomical tissue as actuation advances a plurality of rows of staples through tissue and advances a knife to cut tissue between the rows (lines) of staples. The surgical staplers are mostly multiple use, single patient devices which means the same instrument can be reloaded multiple times with a fresh array of staples in a single surgical procedure. Thus, the stapler can be reloaded with new fasteners once the fasteners have been spent (fired) to provide multiple firings using a single stapler.

Since the staples are contained at the distal end of the stapler, current surgical staplers require distal loading of the staples to achieve multiple firings. This means the clinician needs to remove the entire surgical stapler from the surgical site, i.e., removed not only from the target tissue area but from the patient's body altogether, in order to reload the surgical stapler with fresh fasteners for subsequent application (firing) of staples to tissue. This also requires the user, after loading the new staples, to reinsert and reposition the surgical stapler device back to the target surgical site after each reloading of fasteners. The withdrawal and repositioning of the surgical stapler device adds time and complexity to the procedure, and in certain procedures it might be difficult for the clinician to place the surgical instrument at the exact previous surgical site. Additionally, the withdrawal and repositioning of the instrument becomes time consuming in robotic surgery when the robot arm has achieved fine positioning and the stapler needs to be repositioned each time after the stapler is withdrawn and reloaded.

It would be advantageous to provide a surgical instrument which overcomes the drawbacks associated with current reloading of surgical instruments to achieve multiple firings of a stapler in a single surgical procedure.

SUMMARY

The loading units and instruments of the present invention overcome the deficiencies and disadvantages of the prior art. The present invention advantageously provides loading units and surgical instruments that enable the loading units to be removed and inserted while the instrument remains in the patient's body, thus avoiding the need to remove and reinsert the instrument when additional instrument function is desired.

In accordance with one aspect of the present disclosure, a surgical fastener applier is provided comprising a housing having a proximal opening at a proximal portion and a lumen extending longitudinally distally from the proximal opening and an elongated shaft extending distally from the housing and having a lumen dimensioned to receive a loading unit. The loading unit has an elongated member, first and second jaws at a distal portion and a firing mechanism movable within the elongated member to effect firing of fasteners from the loading unit into tissue clamped between the first and second jaws. The loading unit is insertable into the proximal opening of the housing and through the lumen of the housing and through the lumen of the elongated shaft to expose the first and second jaws from a distal end of the elongated shaft.

In some embodiments, the loading unit includes a cartridge containing the fasteners, the cartridge removable from the loading unit after firing and replaceable with another cartridge having fasteners.

The loading unit can be removed from the surgical fastener applier while the surgical fastener applier remains in a body of a patient. The loading unit in some embodiments is removable by proximal withdrawal from the lumen of the elongated shaft and proximal opening of the housing.

In some embodiments, the housing has a compartment to receive a power pack having a motor and an engagement member removably engageable with the firing mechanism of the loading unit when the power pack is positioned in the compartment to effect powered movement of the firing mechanism from a first position to a second position to fire the fasteners. In some embodiments, the power pack includes a second engagement member removably engageable with an articulating mechanism in the loading unit to effect articulation of the first and second jaws from a linear position to a position angled with respect to a longitudinal axis of the elongated member. The power pack can include a second motor and the second motor can effect linear movement of the articulating mechanism.

In some embodiments, the loading unit is removable and replaceable, while the surgical fastener applier remains in a body of a patient, with a second loading unit having a different structure than the loading unit removed from the surgical fastener applier.

In some embodiments, the loading unit is removable from the surgical fastener applier without removing the surgical fastener applier from the body and a second loading unit having fresh fasteners is loadable into the surgical fastener applier without removing the surgical fastener applier from the body.

In accordance with another aspect of the present disclosure, a loading unit removably loadable into a surgical instrument positioned within a body of a patient is provided. The loading unit includes an elongated member, first and second jaws at a distal portion and a firing mechanism movable within the elongated member to effect firing of fasteners into tissue clamped between the first and second jaws. The loading unit is insertable into a proximal opening of the surgical instrument and through a lumen in a housing and shaft of the instrument while the instrument is positioned in the body of the patient so the first and second jaws extend distally of the shaft of the instrument, the loading unit actuable by the instrument.

The loading unit can be removable from the surgical instrument without removing the surgical instrument from the body. In some embodiments, the loading unit includes a cartridge containing the fasteners and the cartridge is removable from the loading unit after firing and replaceable with another cartridge having fasteners. In some embodiments, the loading unit has an articulation member movable within the elongated member to move the first and second jaws to an angle to a longitudinal axis of the elongated member.

In accordance with another aspect of the present disclosure, a method for reloading a surgical fastener applier is provided comprising the steps of:
a) with the surgical fastener applier maintained in a body of a patient, withdrawing a first loading unit in a proximal direction through a proximal opening in the surgical fastener applier, the loading unit having an elongated member, first and second jaws at a distal portion and a firing mechanism movable within the elongated member to effect firing of fasteners into tissue clamped between the first and second jaws; and
b) with the surgical fastener applier maintained in the body of the patient, inserting a second loading unit in a distal direction through the proximal opening in the surgical fastener applier, the second loading unit having an elongated member, first and second jaws at a distal portion and a firing mechanism movable within the elongated member to effect firing of fasteners into the tissue clamped between the first and second jaws.

In some embodiments, the second loading unit operatively connects to an actuator within the surgical fastener applier for firing the fasteners. In some embodiments, the actuator is powered by a motor, the motor contained in a power pack removably mounted in the surgical fastener applier. In some embodiments, the second loading unit includes an articulation mechanism and the articulation mechanism is engageable with a second actuator within the surgical fastener applier. The second actuator can be powered by a motor, the motor contained in a power pack removably mounted in the surgical fastener applier.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 1B is a top view of the surgical stapler of FIG. 1A;

FIG. 1C is a side view of the surgical stapler of FIG. 1A;

FIG. 1D is a front view of the surgical stapler of FIG. 1A:

FIG. 3A is perspective view of the loading unit of FIG. 2A;

FIG. 3B is a perspective view of an alternate embodiment of the loading unit of the present disclosure;

FIG. 4A is a perspective view of the staple cartridge of FIG. 2A;

FIG. 4B is an enlarged view of the area of detail identified in FIG. 4A;

FIG. 5A is perspective view of the loading unit of FIG. 2A with the staple cartridge not yet loaded into the unit;

FIG. 5B is an enlarged view of the area of detail identified in FIG. 5A;

FIG. 6A is a perspective view of the surgical stapler of FIG. 1A shown extending through tissue;

FIG. 6B is a perspective view similar to FIG. 6A showing the loading unit prior to being loaded into the surgical stapler positioned in tissue;

FIG. 8A is a top view of the motor and drive mechanism (assembly) of the power pack of FIG. 2B (and FIG. 2A) for firing the staples;

FIG. 8B is a side view of the motor and drive mechanism of FIG. 8A;

FIG. 8C is a top view of the power pack of FIG. 2B;

FIG. 8D is a side view of the motor and drive mechanism of FIG. 8A shown engaged with the rod of the firing assembly of the loading unit of FIG. 2A;

FIG. 8E is a perspective view of the motor and drive mechanism of FIG. 8A;

FIG. 8F is a cross-sectional view taken along line G-G of FIG. 8C showing the power pack engaging the firing rod of the disposable loading unit of FIG. 2A;

FIG. 9A is a top view of an alternate embodiment of the power pack to effect both articulation and firing of the surgical stapler;

FIG. 9B is a cross-sectional view taken along line AW-AW of FIG. 9A;

FIG. 9C is a side view of the power pack of FIG. 9A;

FIG. 9D is a cross-sectional view taken along line AT-AT of FIG. 9C;

FIG. 10A is a top view of the motor and drive mechanism (assembly) of the power pack of FIG. 9A for effecting articulation;

FIG. 10B is a side view of the motor and drive mechanism of FIG. 10A;

FIG. 10C is a side view of the motor and drive mechanism of FIG. 10A shown engaged with the articulation rod of the articulation assembly of the loading unit;

FIG. 10D is a perspective view of the motor and drive mechanism (assembly) of FIG. 10A;

FIG. 13A is a side view of an alternate embodiment of the surgical instrument containing the power pack and a proximal loaded disposable loading unit of the present disclosure;

FIG. 13B is a side view of the surgical stapler of FIG. 13A without the loading unit;

FIG. 13C is a side view of the loading unit prior to loading into the surgical stapler of FIG. 13A;

FIG. 14A is a side view of another alternate embodiment of the surgical instrument containing the power pack and a proximal loaded disposable loading unit of the present disclosure;

FIG. 14B is a side view of the surgical stapler of FIG. 14A without a loading unit;

FIG. 14C is a side view of the disposable loading unit prior to loading into the surgical stapler of FIG. 14A;

DETAILED DESCRIPTION OF PREFERRED EMBODIMENTS

The present disclosure provides disposable loading units which can be loaded into surgical instruments without removing the instruments from the body. That is, the loading units are loaded through a proximal opening in the surgical instrument and are engageable with an actuator of the surgical instrument to effect operation of the loading unit. In embodiments disclosed herein, the loading unit is loaded into a surgical fastener applier to apply fasteners to tissue clamped between the jaws of the loading unit. However, it is also contemplated that other loading units performing other functions can be loaded into the surgical instrument in situ. By enabling removal and reloading without removing the instrument from the body, the user does not need to relocate the instrument for each use, e.g., for each firing, which would otherwise be required if the instrument is removed from the surgical site, and reloaded outside the body of the patient. The present disclosure also provides instruments for receiving the loading units and a method for loading the loading units which are described in detail below.

In some embodiments, instead of manual actuation of fastener firing and/or articulation, the loading unit actuation is effected by a battery and power train, which are loadable into a surgical fastener applier (stapler) to power various functions of the loading unit to reduce the forces exerted by the clinician otherwise required if manual force was utilized. The surgical staplers in these embodiments are designed to removably receive the power pack in a compartment or receptacle and the power pack interacts with the loading unit to effect firing of the fasteners, e.g. staples. In some instances, the power pack can be used to effect articulation of the jaw assembly of the loading unit to pivot the jaw assembly with respect to the longitudinal axis of the stapler. The surgical stapler could alternatively have a non-removable power train for effecting firing and/or articulation of the instrument.

Figure 1A:
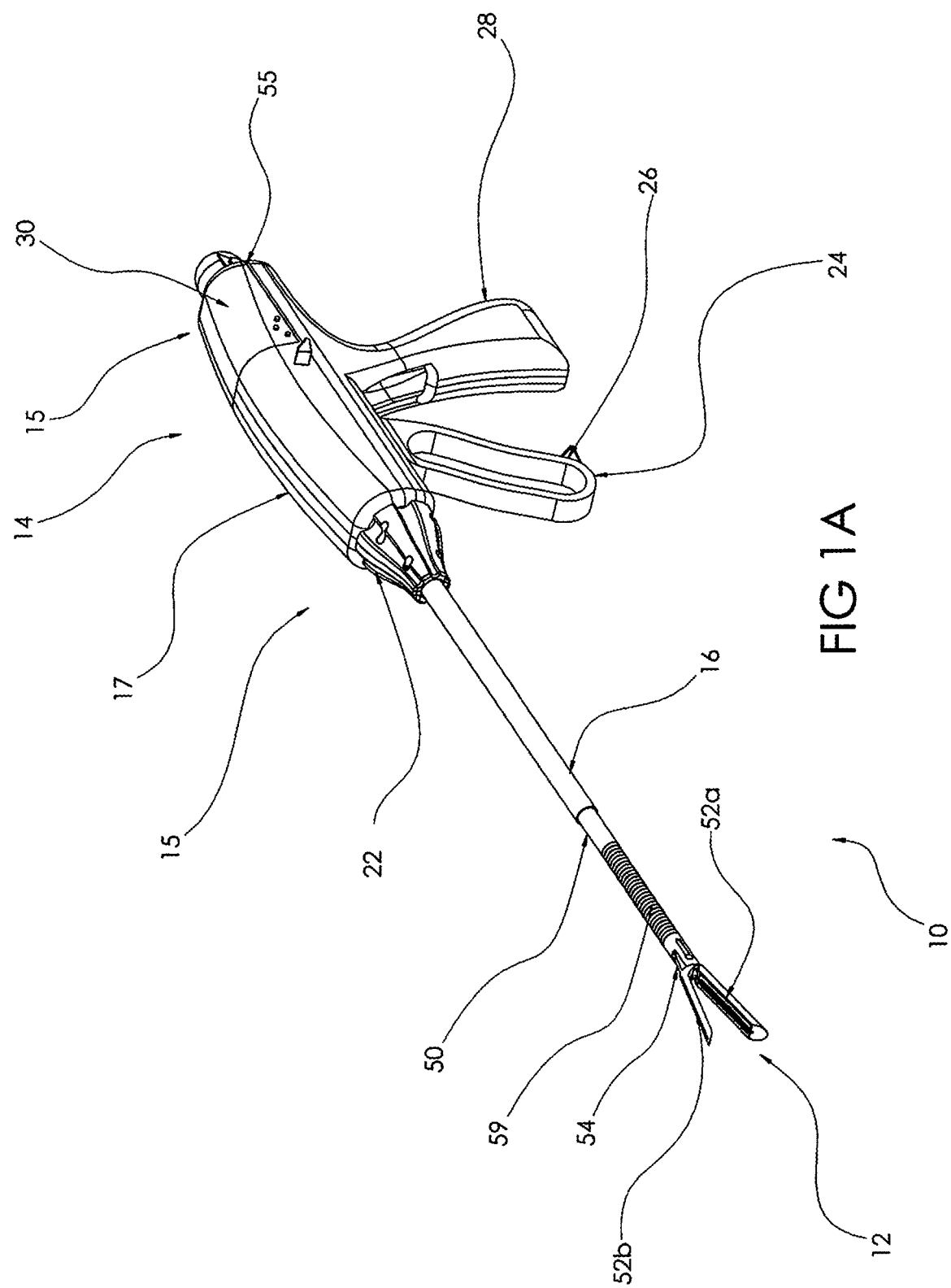
FIG. 1A is a perspective view of a first embodiment of the surgical stapler (fastener applier) of the present disclosure having a proximal loaded loading unit.

The power pack can also be utilized for powering endoscopic linear staplers, such as the stapler depicted in FIG. 1A, other types of staplers as well as other surgical instruments. Examples of these instruments are discussed below.

The loading units (magazines) are preferably disposable. The loading units can be designed/configured for use with endoscopic linear staplers as well as other types of staplers and other types of surgical instruments. Examples of these instruments are also discussed below. The loading units can be used with surgical instruments which are fully manually actuated or fully powered, or with surgical instruments wherein some functions are manually actuated and other functions are powered (e.g., powered by a motor).

When the loading units are used with surgical staplers that dissect and join a given length of tissue, they enable multiple use, e.g., multiple firings, in a single procedure. That is, after the fasteners have been spent, the loading unit is proximally withdrawn from the stapler for loading of a fresh staple cartridge into the removed loading unit or alternatively a new loading unit with a fresh staple cartridge is provided. In either case, the loading unit with fresh staples is proximally loaded into the stapler, i.e., inserted through the back end of the handle assembly, without requiring the time consuming and sometimes difficult reinsertion/repositioning of the surgical stapler at the target site. This reloading of the surgical stapler can be repeated multiple times in the surgical procedure. When reloaded, the loading unit engages the handle assembly of the surgical stapler to interact with the actuators as described below. Thus, during a laparoscopic procedure for example, by removing and reloading the loading unit proximally while maintaining the instrument inside the patient's abdomen, the distal tip of the instrument remains within the field of view of the laparoscopic camera throughout the procedure.

Referring now to the drawings and particular embodiments of the present disclosure, wherein like reference numerals identify similar structural features of the devices disclosed herein, there are illustrated several embodiments of the surgical instruments and removable power packs of the present disclosure.

FIGS. 1A-2A illustrate one embodiment of an endoscopic linear stapler of the present disclosure which is inserted through a trocar (surgical port) and fires linear rows of surgical staples from a cartridge through tissue into contact with an anvil which forms the individual staples. (In some embodiments, the staplers can be inserted without a trocar). The stapler in this embodiment includes an open compartment in the handle housing that enables easy loading of the power pack within the stapler. The stapler could also include a compartment with a cover than is openable and closable as in the openable compartment disclosed in FIG. 2B. In these versions with the cover, the staplers also provide a tight seal to protect the power pack from contaminants so that the power pack does not need to be sterilized for multiple uses.

The power pack is engageable with a staple drive (staple firing) mechanism of the loading unit so that once the power pack and the loading unit are loaded in the stapler, actuation of the motor within the power pack effects firing of the staples through tissue. In some embodiments, the power pack is engageable with an articulation mechanism in the loading unit wherein actuation of the motor effects articulation of the jaw assembly of the loading unit. The powered articulation can be in addition to the powered staple firing or alternatively the stapler could have powered articulation and manual staple firing. A specific embodiment of such powered articulation included with powered firing is shown in FIGS. 9A-10D and discussed in detail below. Note in the embodiments discussed herein, the power pack could be loaded first, followed by insertion of the loading unit or alternatively the loading unit could be loaded first followed by insertion of the power pack.

In the embodiments utilizing a power pack, the power pack with its motor driven mechanism has the advantages of reducing the force requirements of the user which can be high when multiple rows of staples are fired either simultaneously or sequentially from the stapler. The power pack in certain embodiments, such as in FIG. 2B, can be held in a sealed compartment of the stapler, thereby avoiding the need for resterilization and its associated costs and risks, including the risk of damage to the electronic components by heat or chemicals.

The term "surgical fasteners" as used herein encompasses staples having legs which are deformed by an anvil, two part fasteners wherein a fastener or staple component with legs is received and retained in a second component (retainer), and other types of fasteners which are advanced through tissue of a patient in performing surgical procedures.

The term "proximal" as used herein denotes the region closer to the user and the term "distal" as used herein denotes the region further from the user. The terms "top" or "upper" and "bottom" or "lower" refer to the orientation of the instruments as shown in the orientation of the instrument in FIG. 2A, with the compartment for receiving the power pack being on the top and the handle extending at the bottom.

Figure 2A:
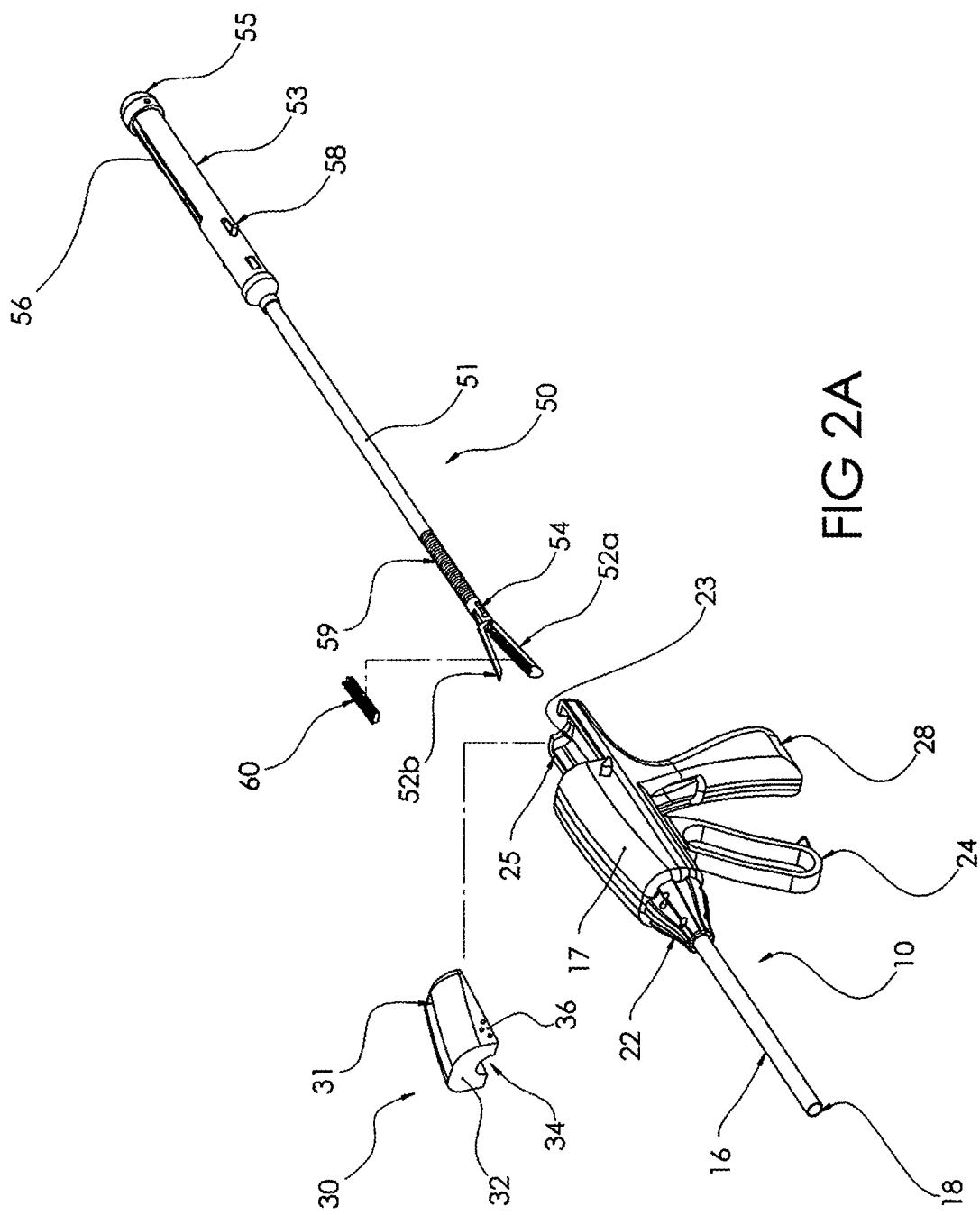
FIG. 2A is a perspective view of the surgical stapler of FIG. 1A showing the surgical stapler with the power pack prior to insertion into the handle compartment and further showing the loading unit and the staple cartridge prior to loading.

Turning initially to FIGS. 1-2A, a first embodiment of the surgical stapler, power pack and loading unit are illustrated. In this embodiment, the power pack, which contains a battery, motor, drive mechanism and stapler engagement structure effects firing of the surgical fasteners (staples).

The surgical stapler, also referred to herein as the surgical fastener applying instrument or surgical fastener applier, is designated generally by reference numeral 10 and includes a proximal portion 14, a distal portion 12 and an elongated or endoscopic portion 16 (also referred to as an elongated tubular portion or shaft) extending between the proximal portion 14 and the distal portion 12. A handle assembly 15 with a housing 17 (also referred to herein as a handle housing) is positioned at the proximal portion 14 and is configured to house and protect internal mechanisms of the stapler and receive the removable power pack when loaded (mounted) therein.

The loading unit 50 (also referred to herein as the disposable loading unit or the magazine) includes an elongated member 51 (also referred to as an endoscopic portion or an elongated tubular member), a handle portion 53 of larger diameter, and a locking knob 55 at a proximal end. At the distal portion are opposing members, i.e., jaws, 52a, 52b, configured to clamp and constrain tissue during operation of the surgical stapler. At least one of the jaws is movable with respect to the other jaw from an open position to receive tissue between the jaws and a closed position to clamp tissue between the jaws. Thus, one of the jaws can be stationary and the other jaw movable with respect to the stationary jaw or alternatively both jaws can move, e.g., pivot, toward each other. In the embodiment of FIG. 1A, both jaw 52b, which contains an anvil with staple forming pockets (staples) and jaw 52a which contains the cartridge supporting the row(s) of surgical fasteners, are movable toward and away from each other. In alternate embodiments, jaw 52b which contains the anvil pockets is movable with respect to non-pivoting (stationary) jaw 52a which contains at least one row of surgical fasteners. In other alternate embodiments, the movable jaw 52b contains the surgical fasteners and the stationary jaw 52a contains the anvil pockets. Jaws 52a, 52b are collectively referred to herein as jaws 52. The fasteners are fired (advanced) from jaw 52a by linear movement of a firing mechanism which engages staple drivers within the jaw 52a which move transverse to the longitudinal axis, i.e., transverse to the direction of movement of the firing mechanism, to sequentially advance (from proximal to distal) the staples in the linear rows of staples from the jaw 52a and through tissue clamped by the jaws 52 to engage the anvil pockets on jaw 52b for formation of the staples. The fasteners can be contained in a separate cartridge 60 which is loaded into jaw 52a prior to insertion of the loading unit 50 into the surgical instrument.

The elongated tubular member 16 of stapler 10 extends distally from the housing 17 and is configured to fit through a surgical port (trocar) used for laparoscopic surgery. The elongated tubular member 16 can be of varying dimensions and in some embodiments is configured to fit through a 10 mm trocar, although other dimensions for fitting through other size trocars are also contemplated such as trocars ranging from 5 mm to 15 mm. It is advantageous to minimize the diameter of the endoscopic portion to minimize the size of the patient's incision. With the jaws 52 in the clamped position, the outer diameter of the elongated member 16 is maintained as the cross-sectional dimension of the closed jaws 52 preferably does not exceed the cross-sectional dimension (i.e., diameter) of the tubular member 16.

The loading unit 50 is inserted in a distal direction through a proximal opening 23 in the housing 17, through a lumen in the housing 17 and through the lumen in elongated member 16, with a portion of shaft 51 and the jaws 52 exiting the distal opening in the lumen of the elongated member 16 so jaws 52 extend distally of the elongated member 16 and are exposed. The loading unit 50 is removable by withdrawing the loading unit in a proximal direction (with the jaws 52 closed) so it is retracted through the lumen in elongated member 16, the lumen in the housing 17 and out the proximal opening 23. In the illustrated embodiment, the power pack 30 has a slot or channel 34 to accommodate the loading unit 50.

The loading unit 50 can in some embodiments include a joint 54 that provides for the articulation of the opposing jaw members 52, i.e., pivoting of the jaw assembly (jaws 52) to angular positions with respect to the longitudinal axis of elongated member 51 of the loading unit so (and thus with respect to the longitudinal axis of shaft 16 of the stapler 10). Articulation can be achieved by linear motion of elongated members extending through the elongated member 51 which are slidable to angle the jaw assembly.

The loading unit has a transverse rod 58 extending from a side of the handle portion 53 of the loading unit 50 to engage an internal wall of the handle assembly. Elongated slot 56 provides an opening for a first engagement member, e.g., flag, of the power pack 30 to engage the firing member which is internal of handle 53 and/or for a second engagement member, e.g., another flag, to engage the articulation member which is internal of handle 53. The elongated member 51 has a laser cut portion 59 proximal of joint 54.

The jaw 52a of proximally loaded loading unit 50, as noted above and illustrated in FIG. 2A, receives a cartridge 60 containing fasteners, e.g., staples. Thus, after firing, the cartridge 60 can be removed and a new cartridge 60 can be loaded into jaw 52a containing staples 66, linear rows of slots 62 to receive the linear rows of staples 66, stapler drivers to advance the staples transversely through the slots and a knife bar 68 (see FIGS. 4A and 4B) advanceable in linear slot 69 to cut tissue between the rows of staples 66. In a preferred embodiment, separate cartridges 60 are loaded into the proximal loading unit 50 after it is withdrawn proximally from the stapler so a single loading unit 50 can receive multiple cartridges 60 (see FIGS. 5A and 5B). In an alternate embodiment, the proximally loaded loading unit can contain a non-removable cartridge so that a new proximal loading unit with a fresh array of fasteners replaces the loading unit with the fired staples. In either embodiment, the loading unit is proximally loaded into the stapler (in a distal direction) and withdrawn proximally from the stapler in situ.

The instrument 10 can include a rotational member or knob 22 engageable with the loading unit 50 and configured to rotate, with respect to the handle assembly, the elongated member 51 and connected jaws 52 about the axis of the elongated member 51, e.g., 360 degree rotation, to change the position of the jaws 52. Articulation can be effected by manual manipulation of a lever adjacent the handle assembly 15. A handle lever 24, linked to an axially movable clamping bar within the loading unit, is pivotable from a first position to a second position closer to stationary handle 26 to effect movement of the jaw 52b and jaw 52a from an open (unclamped) position to a clamping position, also referred to as a closed position of the jaws 52. Release of handle lever 24 returns the jaws 52b, 52a to their open position. A locking lever can be provided to retain the handle 24 in the closed position. Stationary handle 28 for grasping by the user is ergonomically designed for comfort of use. In summary, with a loading unit positioned within the stapler 10, the surgical stapler 10 operates by manual pivoting of the lever 24 toward stationary handle 26, wherein it can be locked by latch 28, to clamp the tissue between jaws 52, followed by powered firing of the staples from jaw 52a, through the clamped tissue and into contact with the staple forming pockets of the anvil of jaw 52b. Prior to firing, the jaws 52 can be rotated to a desired orientation by rotation of endoscopic portion 51 of loading unit 50 via knob 22 and/or articulated about joint 54, via movement of the elongated articulation members, to a desired angled position with respect to the longitudinal axis of elongated portion 51 (and shaft 16). Note articulation can performed by manual manipulation of a lever (not shown) which is operatively connected to an internal elongated member within the loading unit 50 which extends to joint 54. A force applied to the internal elongated member pivots/articulates the jaws 52 about the joint 54. Alternatively, powered articulation can be provided.

The stapler can include a firing lock to maintain the jaws 52a, 52b in an actuation position. The firing lock may be engaged by squeezing the lever 24 of the handle assembly, which thus maintains the distal jaws 52a, 52b in the closed position. Upon completion of tissue joining and dissection, the firing lock may be released by fully squeezing the lever 24 to open jaws 52a, 52b, for example, through spring loading or the like.

In some embodiments the loading unit can be inserted into the stapler and then rotated into a loading position. In these embodiments, the loading unit can include a knob with a locking position that provides an indication to a user that the surgical stapler is properly loaded.

The housing 17 of the handle assembly 15 of the surgical stapler 10 is configured to receive the loadable/removable power pack 30 in receptacle 25. In this embodiment, the power pack housing is not maintained in a sterile environment.

Figure 2B:
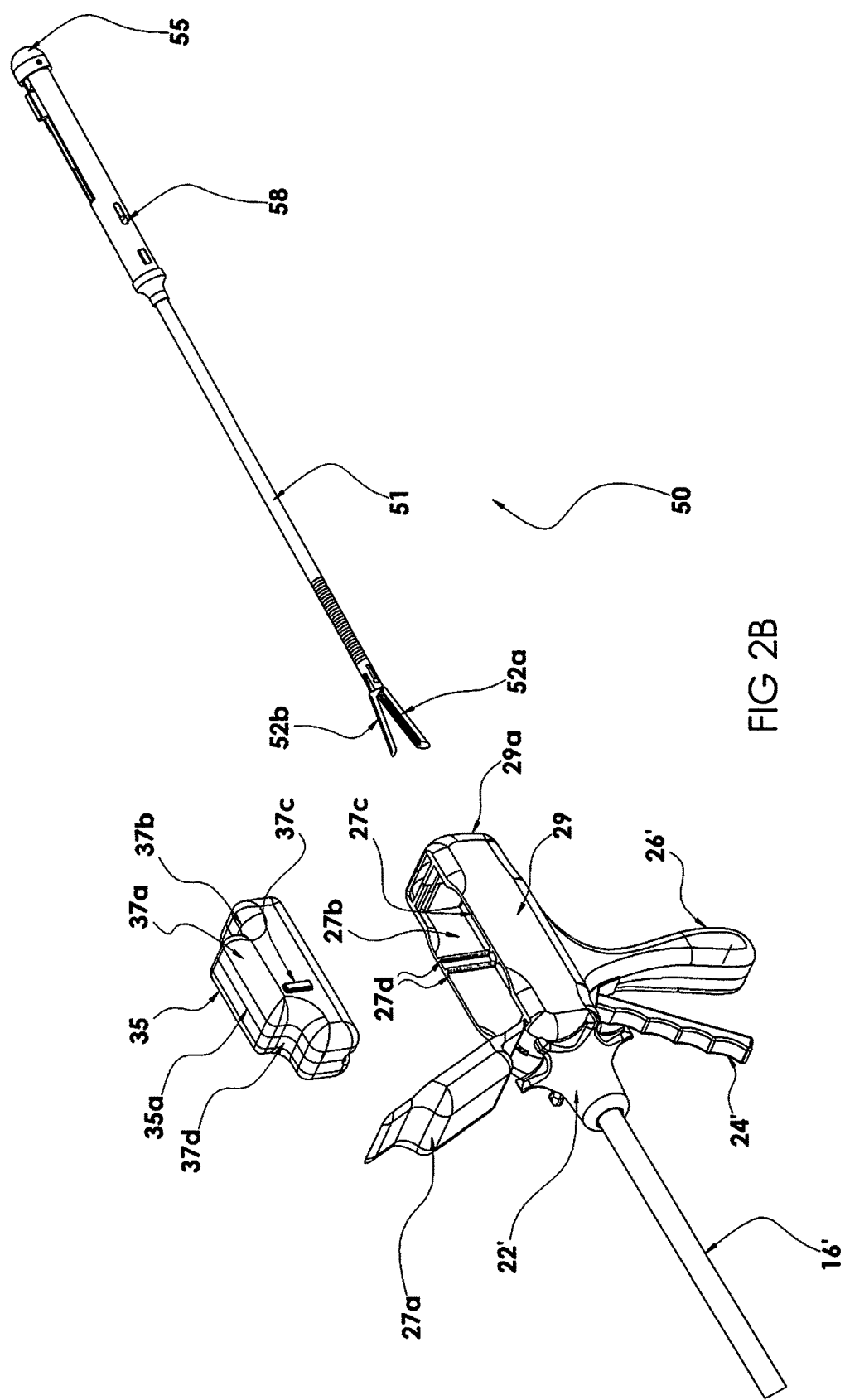
FIG. 2B is a perspective view of an alternate embodiment of the surgical stapler of the present disclosure showing the surgical stapler with the power pack prior to insertion into the handle compartment and further showing the loading unit and the staple cartridge prior to loading.

In the alternate embodiment of FIG. 2B, the power pack 35 is fully contained within a compartment 27b in the handle housing 29 and is therefore maintained in a sterile environment within the surgical instrument so it can be removed and reused in another procedure and/or instrument without the complexities, time, costs and risks of resterilization of the power pack. The sealed environment of the battery and power train within the housing also enables certain features/components to be used which might not otherwise be practical if sterilization of the internal power pack was required. Thus, by preventing contact between the power pack and the patient and/or bodily fluids and the external environment, resterilization is not required in this embodiment.

The receptacle (compartment) 27b includes a base and side walls 27c having one or more guides 27d that cooperate with corresponding guiding structures 37c on the outer wall of the housing 37a of power pack 35 for proper alignment of the power pack 35 in the handle assembly during insertion into the receptacle 27b. In the embodiment of FIG. 2B, the guides 37c on power pack housing 37a are in the form of a pair of ribs or projections 37c extending transversely to a longitudinal axis of the power pack 35 for receipt within grooves formed between guides, e.g., ribs or projections, 27d of the compartment 27b, also extending transversely with respect to a longitudinal axis of the stapler. In the illustrated embodiment, the ribs 37d are on opposing sides of the power pack 35 and are axially offset from each other, although in alternate embodiments they can be axially aligned. Additionally, a different number of ribs (axially or non-axially aligned) can be provided (with corresponding receiving structure in the compartment 27b). It should be appreciated that alternatively, the grooves could be provided on the power pack 35 and the ribs provided on the walls in the compartment 27b to provide the guiding structure for the power pack 35. The guiding structure also helps to retain power pack 35 in position within the compartment 27b. The power pack 35 has rear and front concave regions 37b, 37d to reduce its overall size. The power pack 35 can include a slot or channel (like slot 34 of power pack 30) to receive/accommodate the loading unit 50 so it can be inserted through the proximal opening and endoscopic portion 16' of the stapler. The loading unit 50 is inserted through the proximal opening 29a of the housing 29.

The handle assembly of the stapler includes handles 24' and 26', identical to handles 24, 26 of FIG. 2A, and a rotatable knob 22' identical to knob 22 of FIG. 2A.

A cover 27a for opening and closing the receptacle 27b can be provided. The compartment cover 27a is shown as being hingedly attached to the housing 25, but may alternatively be fully removable or attached in some other manner such as a slidable connection or the like. The cover 27a is shown pivotably mounted to a top portion of the housing 29 (in the orientation of FIG. 2D) for top loading of the power pack, although alternatively, side or bottom loading can be provided. The cover 27a pivots from a closed position to an open position of FIG. 2B to enable loading of power pack 35 into the compartment 27a of the housing 29. In some embodiments, the cover 27a is spring loaded to an open position so it remains open for loading of the power pack 35. Once loaded, the cover 27a is pivoted about its hinge to its closed position. A latch can be provided to latch the cover 27a to the housing 29 in the closed position. When the cover 27a is in an open position, the power pack 35 may be removed from the receptacle 27b or inserted into the receptacle 27b.

In some embodiments, when the cover 27a is in a closed position, the seal of the cover 27a is in contact with the rim of the housing 29 such that the receptacle 27b, and the power pack 35 if inserted into the receptacle 27b, is sealed from the environment exterior to the surgical stapler. The top seal can be attached to the cover 27a and in some embodiments can be in the form of an elastomer that is compressed by the housing, e.g., tightly fits slightly within the housing or is pressed on the rim of the housing 29. In other embodiments, the elastomer seal can be on the housing 29, i.e., extending around the perimeter of the rim of the compartment 27b, and is compressed by the cover 27a to seal between the cover 27a and housing 29. Other seals can also be provided within the surgical stapler to seal/protect the power pack 35 from contaminants, e.g., body fluids. After applications of fasteners and release (unclamping of the jaws from tissue), the cover 27a can be opened and the power pack 35 removed and charged while the stapler and handle assembly are resterilized if the stapler is a reusable instrument or the stapler and handle assembly are disposed of if the stapler is a single use disposable instrument. The power pack 35, due to its sealed configuration discussed above, can be reused without requiring sterilization by insertion into the receptacle of a resterilized handle assembly or a sterile handle assembly of an unused disposable handle assembly.

The power packs 30 and 35 can be used with surgical instruments discarded after use (fully disposable instruments), partially disposable surgical instruments or with fully reusable/sterilizable instruments. The power packs are easily loadable in the surgical instrument, preferably the handle assembly or housing of the instrument, to easily and securely engage structure in the loading unit to effect movement of such structure. The power packs are also easily disengageable from the structure for removal from the housing. The power packs can be configured so they can be loadable and engageable in various types of surgical instruments.

Turning now to the internal components of the power pack 35 of the present disclosure, and with reference to FIGS. 8A-8G, one embodiment of the power pack 35 is shown which includes a motor assembly, battery and electronics contained within housing 35a. (Power pack 30 contains the same components and arrangement as power pack 35) More specifically, the power pack 35 includes a powering assembly including a motor 32 connected to a planetary gear box 34 configured to gear down the output of the motor 32 for proper drive speeds for firing staples from jaw 52a through the tissue into contact with the anvil of jaw 52b. The planetary gear box 34 drives a lead screw 36 through one or more gears operatively connected to the motor shaft. More specifically, upon rotation of the motor shaft by motor 32 in a first direction, gear 38 is rotated in the same first direction, causing rotation of the gear 31 in a second opposite direction due to the intermeshed teeth of gears 31 and 38. Lead screw 36 is operatively connected to gear 31 so that rotation of gear 31 causes rotation of lead screw 36 in the same direction. The power pack 35 includes a battery 33 which can be rechargeable outside the stapler when the power pack 35 is removed. The power pack 35 in some embodiments can include a power switch which is activated, i.e., turned on, by the clinician to start the motor and effect staple firing. In other embodiments, the motor can automatically turn on when the power pack is fully loaded or upon actuation of another control on the stapler housing 17. In some embodiments, the motor can automatically turn off when the power pack is removed from the stapler housing. Note the power pack 35 has a different housing configuration than power pack 30 of FIG. 2A. However, the internal mechanisms are the same.

Connected to the end of lead screw 36 (the end opposite the connection to the gear 31) is a drive mechanism 40. The drive mechanism 40 is configured to move in a linear motion (in an axial direction) along the lead screw 36 in response to rotation of the lead screw 36. For example, the drive mechanism 40 may include internal threads that engage external threads of the lead screw 36 and may include slides engaged in a track that prevent the drive mechanism 40 from rotating and therefore cause the drive mechanism 40 to move linearly (axially) in response to rotation of the lead screw 36. As depicted in FIGS. 8A-8F, the power pack 35 has a compact configuration as the lead screw 36 extends alongside, slightly spaced from, the motor 32 and gear box 34, i.e., both the motor 32/gear box 34 and lead screw 36 extending longitudinally with the lead screw 36 parallel to the motor 32. The drive mechanism 40 is connected to a proximal end of lead screw 36 and extends proximally of the proximal end of the motor 32 in the illustrated embodiment.

The power pack 35 can have features/structure to constrain the motor 32. In the embodiment of FIG. 8F, such feature is in the form of proximal rails 70a and distal rails 70b spaced apart axially within the housing 17. Motor 32 is seated within proximal rails 70a and gear box 34 is seated within rails 70b, the rails 70a, 70b retaining the motor and preventing axial and rotational movement within the housing 17. Bearing or bushings 71a and 71b can also be provided to constrain the lead screw 36 at opposing ends, while allowing rotation thereof, thereby also constraining the motor. Other features can additionally or alternatively be provided to restrain the motor from axial movement while allowing rotation of the lead screw.

The drive mechanism 40 includes a first output flag or yoke 42, which is discussed in more detail below, configured to engage a staple firing mechanism, e.g., firing rod 46, extending longitudinally within the disposable loading unit 50. The staple firing rod 46 extends through the elongated portion 51 of the disposable loading unit 50 and is operatively engageable with a firing rod which is engageable with a series of staple drivers in jaw 52a to advance the fasteners (staples) 66 from the fastener jaw 52a. Alternatively, the firing rod 46 can extend through the elongated portion 51 and itself engage the stapler drivers as the camming surface of the firing rod 46 engages the staple drivers to sequentially fire the staples as the firing rod 46 is advanced. Thus, as the motor 32 generates rotational motion of the lead screw 36 through the planetary gear box 34 and the gears 38, 30, the drive mechanism 40 moves in linear motion along the lead screw 36. Such linear motion effects linear movement of the firing rod 46 (due to the engagement of the boss 44 by the flag 42) which advances the staple driving mechanism to advance (fire) the staples out from jaw 52a through tissue and into contact with the anvil in jaw 52b. As noted above, the firing rod 46 can be a single element extending through the elongated portion 51 (terminating adjacent jaw 52a) or alternatively can be attached to one or more components intermediate the firing rod 46 and jaw 52a.

A clamp bar can be positioned within and concentric with firing rod 46. The clamp bar can be operatively connected to the pivotable handle 24 of stapler 10 via a linkage connecting one end of handle 24 to the distal end of clamp bar. In this manner, movement of pivotable handle 24 toward stationary handle 28 causes the operatively connected jaw clamping mechanism, e.g., the clamp rod, to be advanced distally to pivot jaw 52b toward jaw 52a to clamp tissue between the two jaws 52. Note that for clamping, the clamp bar slides linearly within a lumen of firing rod 46; for staple firing, firing rod 46 moves linearly over the clamp bar.

The power pack 30 or 35 can also include in some embodiments one or more sensors to indicate the position of the firing rod 46 to indicate to the clinician the status of staple firing. For example, a proximal sensor and a distal sensor can be provided in the power pack housing to sense the position of yoke 42 of the drive mechanism 40. Thus, the proximal sensor would sense the initial position of the yoke 42 (and thus the initial position of the firing rod 46) and at the end of the firing stroke, the distal sensor would indicate the end (final) position of the yoke 42 (and thus the final position of the firing rod 46) which would indicate completed firing of the fasteners. The power pack 30 or 35 could also include an audible or visual indicator (viewable though the power pack housing and instrument handle housing) actuated by the sensor to indicate to the clinician the position of the flag 42 and thus the completion or status of the firing stroke to fire the fasteners. The power pack can also include sensors to detect the position of the articulation flag in the embodiments discussed below which have powered articulation. The sensor can include a potentiometer to determine the location during the firing stroke. It can also include an encoder to detect the position along the stroke. Alternatively, the stroke can also be identified by motor count.

It is also contemplated that in alternate embodiments, the sensor(s) can be carried by the handle housing and/or the loading unit rather than (or in addition to) the power pack and utilized to detect the position of the flag 42 and/or firing rod 46 and/or detect the position of the articulation flag and/or articulation rod in the embodiments discussed below which have powered articulation.

It is also contemplated that a sensor(s) can be provided to detect the position of the clamping rod for clamping the jaws. The sensor can be provided in (or supported by) the power pack or alternatively the sensor(s) can be carried by the loading unit and/or by the handle housing rather than (or in addition to) the power pack and utilized to detect the position of the jaws by detecting the position of the flag engaging the jaw clamping rod and/or detecting the position of the jaw clamping rod in the embodiments which have powered clamping.

Note the sensor can be provided in some embodiments; in other embodiments, no sensor is provided.

The output flag 42 of power pack 18, as shown in FIG. 8D, is configured to engage a bossed end 44 of the firing rod 46 of the loading unit 50 when the power pack 18 is fully inserted into the receptacle 27b of the handle assembly 17. As shown, the output flag (yoke) 42 has a receiving or mounting feature or member (also referred to as the engagement feature (member) or firing rod engagement feature (member) in the form of two arms 43a and a slot 43b therebetween, configured to frictionally (and releasably) engage the bossed end 44, the feature aligning with the bossed end 44 during insertion. (The aforedescribed guiding structure on the power pack 35 and internal wall of the compartment 27b aid such alignment). Note the firing rod 46 is able to rotate when the first output flag 42 of the power pack 35 is engaged with the bossed end 44. When the power pack 35 is secured to the firing rod 46 by the first output flag 42, linear motion generated at the first output flag 42 by the motor actuated drive assembly is transferred to the firing rod 46, which moves linearly to actuate the staple firing mechanism. That is, rotation of the gear 30 effects axial (linear) movement of the drive screw 36 which effects axial (linear) movement of the connected drive mechanism 40 to effect axial (linear) movement of the associated drive mechanism (rod) engaging member (i.e., flag 42). It should be appreciated that flag 42 provides one example of the releasable attachment (engagement member) of the motor assembly to the firing rod 46, it being understood that other mounting (engagement) members or features are also contemplated to engage the firing rod to advance it axially.

Figure 7A:
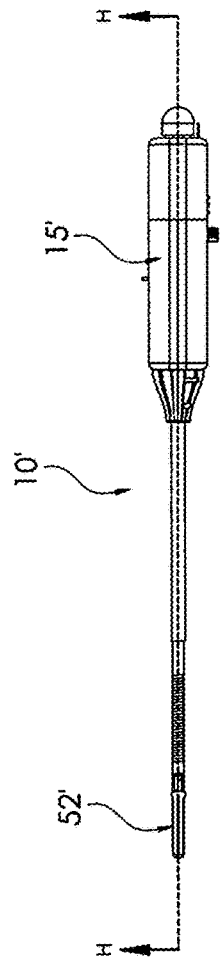
FIG. 7A is a top view of an alternate embodiment of the stapler of the present disclosure.
Figure 7B:
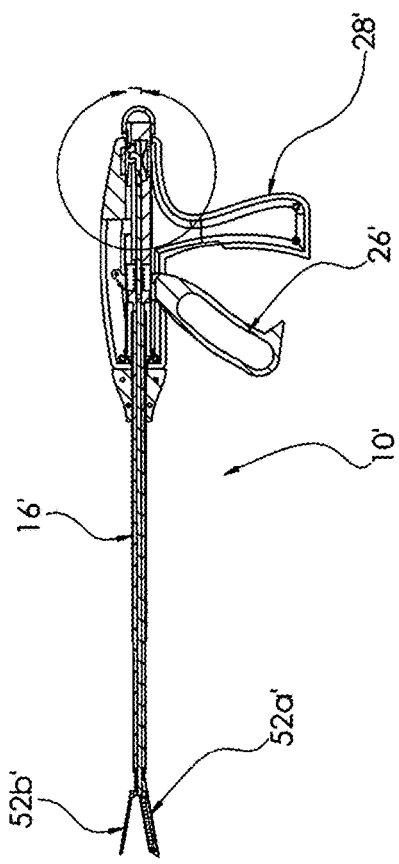
FIG. 7B is a cross-sectional view taken along line H-H of FIG. 7B.
Figure 7C:
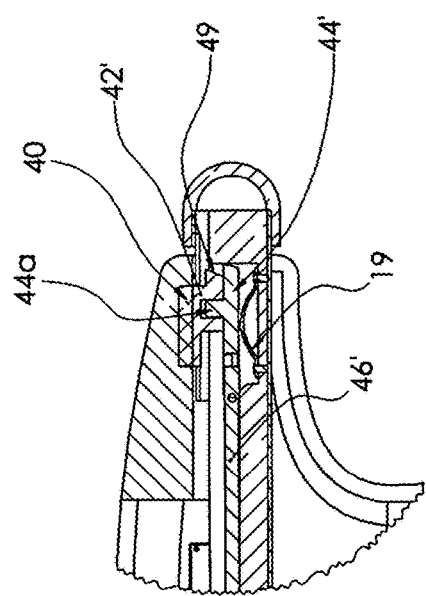
FIG. 7C is a close up view of the area of detail identified in FIG. 7B.

In the alternate embodiment of FIGS. 7A-7C, the bossed end 44', when the loading unit 50 is sufficiently inserted into the stapler, engages edge 49 of output flag 42' (which is identical in structure and function to output flag 42 except for the angled edge 49), which biases the bossed end 44' downwardly to compress spring 19 within the handle housing of the stapler. After boss 44a passes edge 49 and is aligned with the recess/slot in the flag 42, it is biased upwardly (in the orientation of FIG. 7C) toward the recess/slot by the spring 19 for engagement by the flag 42' as shown in FIG. 7C so the firing rod of the loading unit is engaged with the drive mechanism of the power pack. Note, in this embodiment, the bossed end 44' is a separate piece attached to rod 46' which effects firing in the same manner as rod 46. In an alternate embodiment, the bossed end 44' and rod 46' can be one piece. In all other respects, the stapler 10' of FIG. 7A is the same as stapler 10 of FIG. 1A and corresponding parts (which have the same structures and functions) have been labeled with "prime" designations for convenience.

In the embodiment of FIGS. 1-8F, the proximal loading unit 50 is used with a stapler 10 receiving a power pack 35 that actuates the firing rod 46 to fire the staples while other steps are performed manually. In summary, in this embodiment, in use, the jaws 52a, 52b are moved to the closed (clamped) position manually by a hand actuated lever or control, e.g., handle 24. Also, in this embodiment, the jaws 52 are articulated with respect to the longitudinal axis of the endoscopic portion manually by a hand actuated lever or control. Thus, the clinician would manually clamp the jaws, manually rotate the endoscopic portion and attached jaws 52, and manually articulate the jaws by manipulation of controls at the proximal end of the stapler 10, e.g., at the handle 15.

Figure 15:
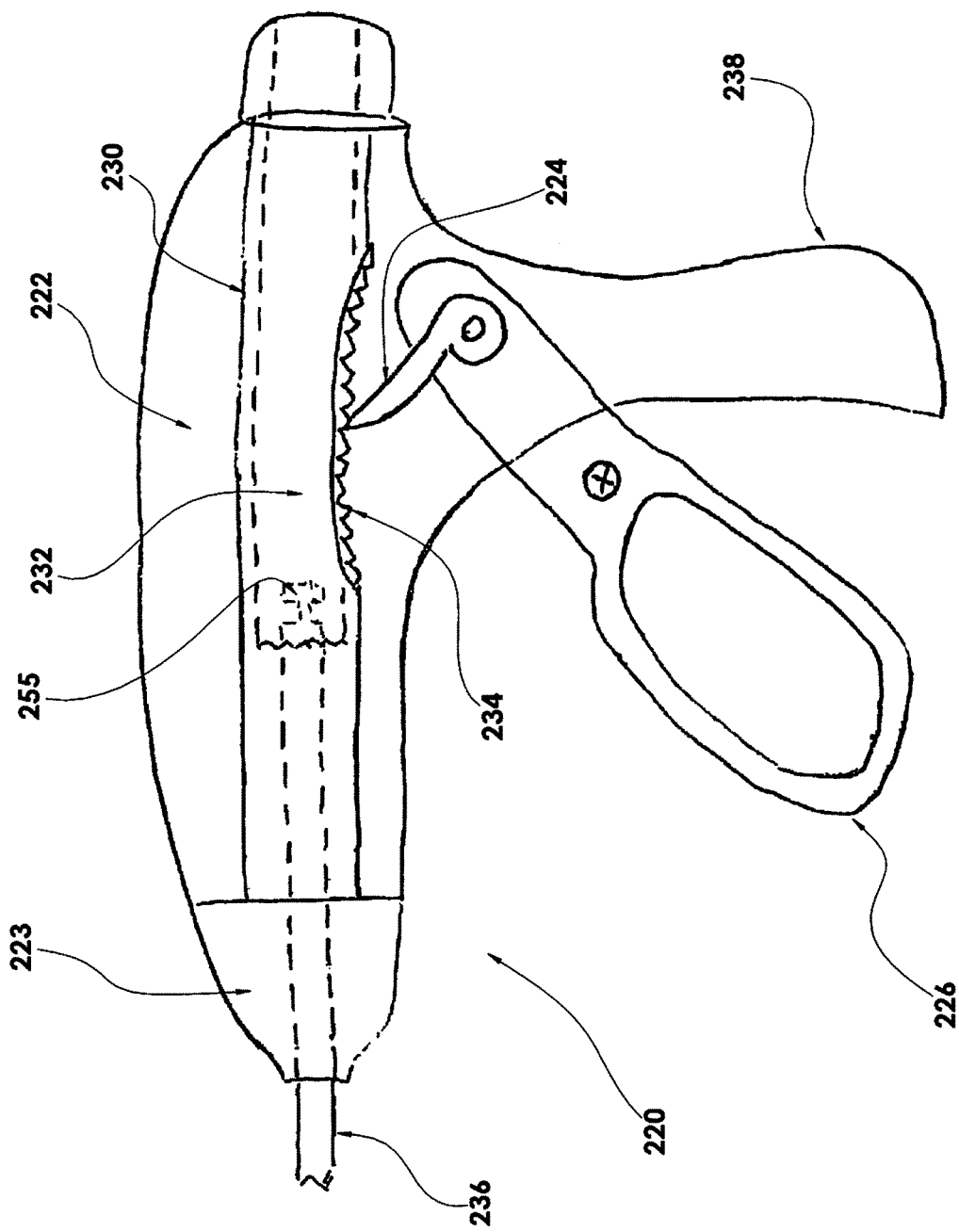
FIG. 15 is a side view of an alternate embodiment of the surgical stapler having manual firing.

It is also contemplated that the proximal loading unit can be used with a stapler wherein all or some of the steps/functions are manually actuated, i.e., clamping, articulation, and firing. An example of this is shown in FIG. 15. Stapler 220 has a pawl 224 within the handle housing 222. Loading unit 230 includes an engagement member 232 having a rack 234 engageable with the pawl 224. Engagement member 232 is operatively connected to deployment/firing rod 236 at connection 235. When handle 226 is moved toward handle 228, due to the pawl/rack engagement at connection 235, the engagement member 232 moves distally thereby causing the deployment (firing) rod 236 to move distally to fire the fasteners in the same manner as rod 46 described above. Stapler 220 can include a rotation knob 223 which functions like knob 22. The loading unit 230 in all other respects is identical to the loading unit 50 and like loading unit 50 has a pair of jaws for clamping tissue with one jaw receiving the fasteners and an opposing jaw having an anvil. The loading unit can also provide for articulation of the jaws as in the aforedescribed embodiments. Note the stapler 220 of FIG. 15 can be used to manually actuate loading units having other configurations such as the alternate loading units and alternate jaw assemblies disclosed herein.

In some embodiments, the seal inside the tubular member, e.g., tubular member 16, of the surgical stapler maintains positive pressure so that the loading unit may be removed and reloaded during use. The seal may be, for example, a silicone seal or the like. Additionally, since the seal maintains positive pressure, the tubular member of the surgical stapler may, advantageously, itself function in certain instances as a trocar for use with other surgical tools.

In some embodiments, the handle lever 24 may have a mechanism operatively connected thereto that interacts with the loading unit 50 to prevent the lever 24 from being actuated, for example, by squeezing by a user, if the loading unit is not properly loaded into the surgical stapler. Additionally, in some embodiments, a user will advantageously be able to determine if the loading unit 50 is properly loaded into the surgical stapler via an alignment feature on the knob 55 of the loading unit 50 configured to indicate proper loading of the loading unit after sufficient insertion through the proximal entry opening 23 of the stapler such that the knob 55 enters a locking position. The locking mechanism may be configured to generate an indication to a user when the loading unit is in the locking position, such as an audible sound, tactile feedback, or the like, thereby indicating to a user that the surgical stapler is properly loaded. For instance, the loading unit 50 may be pushed against a spring force generated by a mechanism in the surgical stapler. (Note that the mechanism of FIG. 7C described herein could provide such audible or tactile feedback due to the spring action) Once in the locking position, the loading unit 50 can be retained until the locking mechanism is engaged to release the loading unit.

FIG. 1A shows one embodiment, of an endoscopic linear stapler that can have proximal loaded loading unit of the present disclosure, and FIGS. 6A and 6B show the endoscopic linear stapler extending through a trocar T passing through tissue A. (FIG. 6B shows loading unit 50 prior to insertion in a distal direction through the handle and endoscopic portion 16 of the stapler 10). However, the loading unit of the present disclosure is not limited to such endoscopic linear staplers. For example, FIGS. 14A-14C illustrate another endoscopic linear stapler, designated by reference numeral 120, that can utilize the loading unit of the present disclosure. The stapler 120 can be manually actuated or can receive and be powered by the power pack 30 or 35. Stapler 120 has a handle 132 manually pivotable towards stationary handle 130 for clamping of the jaws, an endoscopic portion or shaft 124 extending from the handle housing 128, and a loading unit 121 with a jaw assembly containing jaws 122a, 122b at a distal portion of elongated member 125. The endoscopic portion 124 is flexible which enables use in various endoscopic procedures. In some embodiments, the flexible endoscopic portion 124 can be stretched to make it more rigid to facilitate insertion of the loading unit 121 through the lumen in the endoscopic portion 124. The stapler 120 also includes a rotation knob 126 for rotation of the elongated portion 123 of loading unit 121 to rotate the jaws 122a, 122b. Power pack 35 is shown fully loaded (inserted) within the handle housing 128 and the cover 129 closed to seal the power pack 35 from the external environment. As in the embodiment of FIGS. 8E-8F, the flag 42 extending from lead screw 36 engages a firing rod within the elongated member 125 of loading unit 121 to effect movement of the flexible firing rod to fire the staples when the motor of the power pack 35 is actuated. Power pack 90 having articulation described below can also be utilized with stapler 120. Manual firing and/or manual articulation rather than powered are also contemplated.

In use, the loading unit 121 is inserted in a distal direction through a proximal opening in the stapler and through a lumen in the handle housing 128 to extend through the lumen in endoscopic portion 124. As noted above, the endoscopic portion can be stiffened prior to insertion of the loading unit 121 so it assumes a more linear position to facilitate insertion of the loading unit 121. (The loading unit 121 could also be stiffened prior to insertion if it is provided with a flexible elongated member). The power pack 35 engages the loading unit 121 in a similar manner as engagement with loading unit 50. As with loading unit 50, after staple firing, the loading unit 121 can be removed by proximal withdrawal (retraction) through the endoscopic portion 124 and through the handle housing 128 and proximal opening for replacement with another loading unit with fresh staples, or replacement of the same loading unit with a fresh cartridge, for proximal loading into the stapler 120. As noted above, the insertion (loading) and reloading with fresh staples can be achieved while the instrument remains in position, i.e., without moving the instrument from its location in the body and/or without withdrawing the instrument from the patient.

The loading unit is also not limited to use with endoscopic linear staplers, nor is it limited to use with staplers. FIGS. 13A and 13B illustrate one example of a different stapler with a proximally loaded loading unit. As in the endoscopic linear staplers discussed herein, these staplers can also have a knife bar to cut tissue between the rows of staples applied to the tissue.

By way of example, a proximal loaded loading unit can be used with a circular stapler that applies circular arrays of staples such as shown in FIGS. 13A-13C. Surgical stapling instrument 100 can be manually powered or can receive and be powered by the power pack 35 or 30 of the present disclosure. Stapler 100 has a handle 117 manually pivotable towards stationary handle 118 for clamping of the jaws, an elongated tubular portion or shaft 112 extending from the handle housing 116 and a disposable loading 101 with a jaw assembly having an anvil (jaw) 102 and a cartridge (jaw) 106 containing circular arrays of fasteners (staples). The anvil 102 has a proximal clamping surface 108 and is movable by anvil rod 104 toward the cartridge 106 to clamp tissue between the anvil clamping surface 108 and distal clamping surface 110 of cartridge 106 by manual movement of handle 117 toward stationary handle 118. The stapler 100 also includes a rotation knob 114 for rotation of the elongated portion (shaft) 105 of the loading unit 101 to rotate the jaws 102, 106. Power pack 35 is shown fully loaded (inserted) within the handle housing 116 and the cover is shown closed to seal the power pack 35 from the external environment. As in the embodiment of FIGS. 8A-8F, the flag 42 extending from lead screw 36 engages a firing rod within the loading unit 101 to effect movement of a firing rod extending through elongated portion 105 to fire the circular arrays of staples when the motor of the power pack 35 (or 30) is actuated. Power pack 90 having articulation described below can also be utilized with stapler 100. Manual firing and/or articulation is also contemplated. In use, the loading unit 101 is inserted through a proximal opening in the stapler 100 and through a lumen in the handle housing to extend through the lumen in elongated portion 112. As with loading unit 50, after staple firing, the loading unit 101 can be removed by proximal withdrawal (retraction) through the elongated portion 112, the handle housing 116 and the proximal opening for replacement with another loading unit with fresh staples, or replacement of the same loading unit with a fresh cartridge and in some embodiments a fresh anvil, for proximal loading (in a distal direction) into the stapler 100. As noted above, the insertion (loading) and reloading can be achieved while the instrument remains in position, i.e., without moving the instrument from its location in the body and/or without withdrawing the instrument from the patient. The anvil 102 can be tiltable as it is inserted through the housing 116 and elongated portion 112 to facilitate insertion. The cartridge 106 can also be tiltable for insertion. The anvil 102 and/or cartridge 106 can alternatively or in addition be collapsible and expandable to facilitate insertion through the elongated portion 112.

In the embodiments of FIGS. 8A-8F, a gear mechanism is driven by the motor to rotate the lead screw to advance the drive mechanism to effect firing of the staples. In the alternate embodiments of FIGS. 11A-12B, a belt drive mechanism is used to effect firing. The belt drive mechanism is contained in the power pack 35 or 30 (or 90) in the same manner as the gear mechanism of the foregoing embodiments, and thus the power pack for the belt drive would include the housing 35*a* of the configuration of FIG. 2B or housing 31 of the configuration of FIG. 2A and loaded in the stapler in the same manner as the power packs described above. The belt drives of FIGS. 11A-12B are described below for use with the stapler of FIG. 1A but can be used in the other surgical staplers and instruments disclosed herein which are designed to receive power pack 30, 35 or power pack 90 for powered actuation.

Figures 11A, 11B:
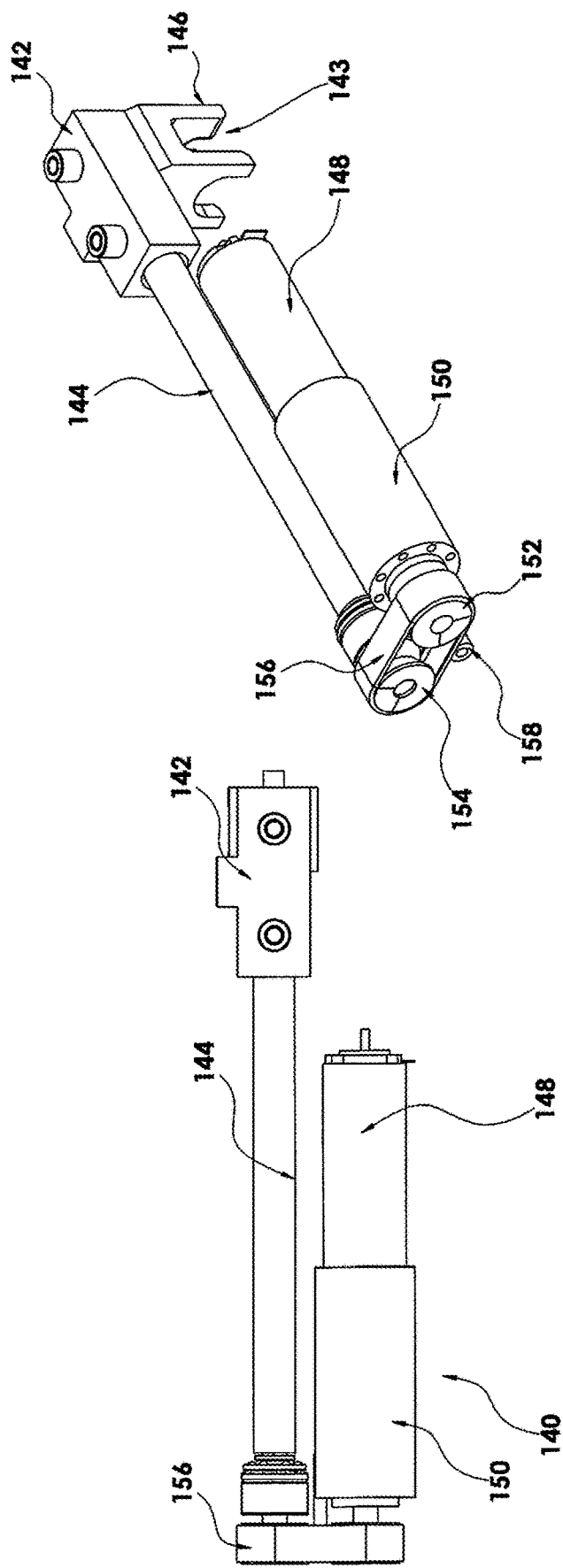
FIG. 11A is a perspective view of the motor and drive mechanism (assembly) of the power pack of an alternate embodiment having a belt drive.
FIG. 11B is a top view of the motor and drive mechanism (assembly) of FIG. 11A.

Turning first to the embodiment of FIGS. 11A-11B, the belt drive assembly (mechanism) includes a motor 148 connected to a planetary gear box 150 configured to gear down the output of the motor 148 for proper drive speeds for firing staples from jaw 52*a* through the tissue into contact with the anvil of jaw 52*b*. The planetary gear box 150 drives a lead screw 144 via the drive belt operatively connected to the motor shaft. More specifically, upon rotation of the motor shaft by motor 148, first rotatable disc 152 (also referred to as the first wheel or pulley) is rotated in a first direction, causing movement of belt 156 and rotation of second rotatable disc 154 (also referred to as the second wheel or pulley). Note the two discs 152, 154 are spaced apart and not in contact. Lead screw 144 is operatively connected to disc 154 so that rotation of disc 154 causes rotation of lead screw 144 in the same direction. The power pack 35 (or 30) includes a battery which can be rechargeable outside the stapler when the power pack 35 is removed. The motor 148 is actuated in the various ways described above with regard to power pack 35 of FIG. 8C. A tensioner can be provided such as tensioner 158, illustratively in the form of a tension disc or wheel, to apply a force against the belt 156. In the orientation of FIG. 11A, the tensioner 158 is positioned underneath the drive belt 156 and applies an upward tensioning force against the belt 156 in a direction toward discs 152, 154. Other types of mechanisms to apply a tensioning force to the belt are also contemplated for use in the embodiments of FIGS. 11A-12B if such tensioning of the drive belt 156 is desired.

Connected to the end of lead screw 144 (the end opposite of the connection to the disc 154) is a drive mechanism 142. The drive mechanism 142, like drive mechanism 40 of FIG. 8A, is configured to move in a linear motion (in an axial direction) along the lead screw 144 in response to rotation of the lead screw 144. For example, as in the drive mechanism 40, drive mechanism 142 may include internal threads that engage external threads of the lead screw 144 and may include slides engaged in a track that prevent the drive mechanism 142 from rotating and therefore cause the drive mechanism 142 to move linearly in response to rotation of the lead screw 144. As shown, the lead screw 144 extends alongside, slightly spaced from, the motor 148 and gear box 150, i.e., both the motor 148/gear box 150 and lead screw 144 extending longitudinally with the lead screw 144 parallel to the motor 148. The drive mechanism 142 extends proximally of the proximal end of the motor 148 in the illustrated embodiment.

The drive mechanism 142, like drive mechanism 140 of FIG. 8E, includes a first output flag or yoke 146 with slot 143 configured to engage a staple firing rod 46 of the loading unit 50 extending longitudinally within the handle 4. The flag 146 is the same as flag 42 of FIG. 8E and engages the staple firing rod 46 in the same manner as flag 42. Therefore, for brevity, further discussion of flag 146 and it engagement with firing rod 46 is not provided as the structure and function of flag 42, and alternative firing rod engagement features, are fully applicable to flag 146 of FIGS. 11A-11B. In brief, as the motor 148 generates rotational motion of the lead screw 144 through the drive belt, the drive mechanism 144 moves in linear motion along the lead screw 144 to effect linear movement of the firing rod 46 which advances the staple driving mechanism to advance (fire) the staples out from jaw 52*a* through tissue and into contact with the anvil in jaw 52*b*.

In an alternate embodiment of a belt drive mechanism, the belt drive mechanism can have different sized discs (wheels). That is, one disc which is operatively connected to lead screw 144 is larger in diameter than other disc. Consequently, instead of providing a one to one ratio of the discs as in discs 154 and 152 of FIG. 11A, a greater ratio of disc to disc is provided which varies the output of motor 168. That is, the rotational output of lead screw 144 is less than the rotational output of the motor shaft due to the differing degree of rotation due to the varying sizes. An example of such different sized discs is shown with the alternate belt drive mechanism of FIGS. 12A and 12B.

Figures 12A, 12B:
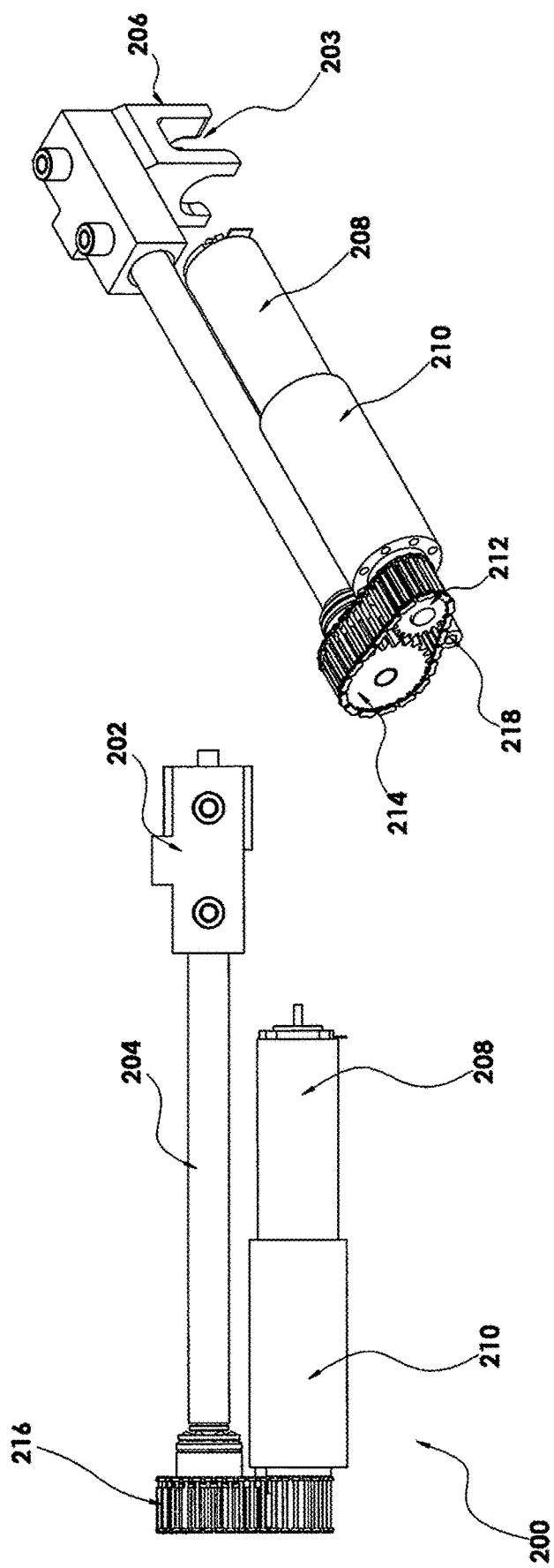
FIG. 12A is a perspective view of the motor and drive mechanism (assembly) of the power pack of another alternate embodiment having a belt drive.
FIG. 12B is a top view of the motor and drive mechanism of FIG. 12A.

FIGS. 12A-12B illustrate an alternate embodiment of a belt drive mechanism. The belt drive 200 differs from the belt drive of FIG. 11A in that discs 212, 214 have teeth to engage ribs or treads on belt 216. As shown, the toothed discs 212, 214 are spaced apart so their teeth/projections do not intermesh—the teeth of disc 212 engage belt 216 and the teeth of disc 214 engage belt 216. Rotation of disc 212 moves drive belt 216 in the same direction due to its engagement with the teeth, which causes rotation of toothed disc 214 in the same direction due to engagement with its teeth to rotate lead screw 204. In all other respects, mechanism 200 is identical to mechanism 140.

Belt drive mechanism (assembly) 200 has a motor 208 connected to a planetary gear box 210 configured to gear down the output of the motor 208. The planetary gear box 210 drives a lead screw 204 through the belt drive operatively connected to the motor shaft. Upon rotation of the motor shaft by motor 208, first disc (wheel or pulley) 212 is rotated in a first direction, causing movement of belt 216 and rotation of second disc (wheel or pulley) 214. Lead screw 204 is operatively connected to disc 214 so that rotation of disc 214 causes rotation of lead screw 204 in the same direction. A tensioner 218 like tensioner 158 can be provided to apply tension to the belt 216. The drive mechanism 202, like the drive mechanism 142 of FIG. 11B, includes a first output flag or yoke 206 with slot 203 configured to engage a staple firing rod 46 of the proximal loading unit in the same manner as flag 42. Rotation of the motor shaft generates rotational motion of the lead screw 204 through the drive belt, causing the drive mechanism 202 to move in linear motion along the lead screw 204 to effect linear movement of the firing rod 46 which advances the staple driving mechanism to advance (fire) the staples out from jaw 52*a* through tissue and into contact with the anvil in jaw 52*b*.

The second toothed disc 214 which is operatively connected to lead screw 204 is larger in diameter than first toothed disc 2122. Consequently, instead of providing a one to one ratio of the discs as in discs 154, 152, a greater ratio of disc 214 to disc 212 is provided which varies the output of motor 208. That is, the rotational output of lead screw 204 is less than the rotational output of the motor shaft due to the differing degree of rotation of discs 214, 212 due to the varying sizes. It should be appreciated that in alternative embodiments, the toothed discs 212 214 can be the same size as in the embodiment of FIG. 11A.

It should be appreciated that the foregoing belt drive mechanisms can be used as an alternative to the gear mechanism in power pack 30 or 35 as well as an alternative to one or both of the gear mechanisms of power pack 90 discussed herein.

In the foregoing embodiments, the power packs 30 and 35 were described for powering staple firing. In an alternate embodiment, the power pack can include a drive mechanism for effecting articulation. This motor powered articulation can be in addition to the motor powered staple firing, or alternatively, the power pack can be used solely for powered articulation. The embodiment of FIGS. 9A-10D illustrate a power pack which powers both staple firing and articulation. If only for articulation, the power pack described herein (power pack 90) would not include the gear mechanism engageable with the firing rod 46 for staple firing.

The power pack 90 can be loaded in the staplers disclosed herein in the same manner as power pack 35 and 30, however, the engagement features of the power pack 90 engage both the firing rod of the loading unit, e.g., loading unit 50, as well as the articulation rod of the loading unit. In the illustrated embodiment, the power pack 90 is shaped like power pack 35 and can have guides e.g., projections 90a, 90b, either axially aligned or axially offset, similar to guides 37c of power pack 35 for alignment with guiding structure in the compartment of the stapler More specifically, the power pack has a motor assembly and drive mechanism for firing staples which is identical to that of the power pack 35 of FIG. 2B. However, power pack 90 differs from power pack 35 (and power pack 30) in that it additionally has a motor assembly and drive mechanism for articulating the jaws of the loading unit. The addition of the articulation assembly can be appreciated by a comparison of the cross-sectional view of FIG. 8F, which only effects firing of the fasteners (staplers), and the cross-sectional view of FIG. 9D which effects firing of fasteners and articulation of the jaw assembly.

The powered staple firing assembly like the firing assembly of power pack 35 of FIG. 8F, includes a motor 83 connected to a planetary gear box 85 configured to gear down the output of the motor in the same manner as motor 32 and gear box 34 of power pack 35. The planetary gear box 85 drives a lead screw 86 through one or more gears operatively connected to the motor shaft. Upon rotation of the motor shaft by the motor 83 in a first direction, gear 81 is rotated in the same first direction, causing rotation of the gear 84 in a second opposite direction due to the intermeshed teeth of gears 81 and 84. Lead screw 86 is operatively connected to gear 84 so that rotation of gear 84 causes rotation of lead screw 86 in the same direction. The power pack 90 includes a battery 33 which can be rechargeable outside the stapler when the power pack 90 is removed. The power pack 90 in some embodiments can include a power switch which is activated, i.e., turned on, by the clinician to start the motor and effect staple firing. In other embodiments, the motor can automatically turn on when fully loaded or upon actuation of another control on the stapler housing.

Connected to the end of lead screw 86 (the end opposite the connection to the gear 84) is a drive mechanism 80 which is configured to move in a linear motion (in an axial direction) along the lead screw 86 in response to rotation of the lead screw 86. Drive mechanism 80 includes a flag or yoke identical to yoke 42 of power pack 35 discussed above, which engages the flange or boss 44 of firing rod 46 within the loading unit. The connection of the flag to the firing rod, the motor and gear mechanism, and the drive mechanism 80 of power pack 90 are the same as the power pack 35 and therefore the aforedescribed functions and features/components of power pack 35 for staple firing are fully applicable to the function and features/components of power pack 90 for staple firing so for brevity are not fully repeated herein. It should also be appreciated that the alternative mechanisms for motor powered stapled firing, such as the various belt drive mechanisms discussed above and/or illustrated in the Figures, can also be used in the power pack 90 to effect staple firing. Additionally, the various sensors discussed above with regard to sensing the firing stroke can also be provided in power pack 90 for the same uses.

Power pack 90 also has an articulation assembly that includes a powering assembly including a motor 96 connected to a planetary gear box 93 configured to gear down the output of the motor 96. The planetary gear box 93 drives a lead screw 98 through gears 91, 92 operatively connected to the motor shaft. More specifically, upon rotation of the motor shaft by motor 96 in a first direction, gear 91 is rotated in the same first direction, causing rotation of the gear 92 in a second opposite direction due to the intermeshed teeth of gears 92 and 91. Lead screw 98 is operatively connected to gear 92 so that rotation of gear 92 causes rotation of lead screw 98 in the same direction. The power pack 90 in some embodiments can include a power switch which is activated, i.e., turned on, by the clinician to start the motor and effect articulation.

Connected to the end of lead screw 98 (the end opposite the connection to the gear 92) is a drive mechanism 95 configured to move in a linear motion (in an axial direction) along the lead screw 98 in response to rotation of the lead screw 98. For example, the drive mechanism 95, like drive mechanism 40 described above, may include internal threads that engage external threads of the lead screw 98 and may include slides engaged in a track that prevent the drive mechanism 95 from rotating and therefore cause the drive mechanism 95 to move linearly (axially) in response to rotation of the lead screw 98. As depicted, the power pack 90 has a compact configuration as the lead screw 98 extends alongside, slightly spaced from, the motor 96 and gear box 93, i.e., both the motor 96/gear box 93 and lead screw 98 extending longitudinally with the lead screw 98 parallel to the motor 96. The drive mechanism 95 is connected to a proximal end of lead screw 98. The drive mechanism 95 has an articulation rod engagement feature in the form of a flange or yoke 94 extending therefrom having legs 99b and a recess 99a to engage an articulation rod 79 movable within the elongated member 51 of the loading unit. In the illustrated embodiment, the articulation rod 79 includes a flange or boss 78 which is engageable by the flag 94. The output flag 94 can engage the bossed end 78 of the articulation tube 79 in substantially the same manner as the output flag 42 engages the bossed end 44 of the firing rod 46 as discussed above.

The articulation assembly of the power pack 90 is oriented in the opposite direction from the staple firing assembly to minimize the space required in the power pack 90, thereby providing the power pack with a compact configuration. As can be appreciated by reference to FIG. 9D, the drive assembly 80 and associated flag 82 are at a proximal end of the assembly for firing staples with the lead screw 86 extending distally toward the gears 81, 84. The driving assembly 95 with associated flag 94 of the assembly for articulation are at a distal end with the lead screw 98 extending proximally toward gears 91, 92. Also, as can be appreciated by reference to the orientation of FIG. 9D, the articulation assembly is above the firing assembly, and the articulation assembly in the illustrated embodiment is positioned axially proximal of gears 81, 84 and axially distal of drive mechanism 80, radially spaced from lead screw 86.

The power pack 90, like power pack 35 can have features/structure to constrain the motors 84 and 96. These include for example spaced apart proximal and distal rails like proximal and distal rails 97a, 97b of FIG. 9B, wherein gear box 93 can be seated within the proximal rails and the motor can be seated within the distal rails, the rails retaining the motor and preventing axial and rotational movement within the housing of power pack 90. Bearing or bushings like bushings 71a, 71b of FIG. 8F can also be provided to constrain the lead screw 98 at opposing ends, while allowing rotation thereof, thereby also constraining the motor. Other features can additionally or alternatively be provided to restrain the motor from axial movement while allowing rotation of the lead screw.

Upon loading of the power pack 90, the flag of the drive mechanism 80 of the staple firing assembly engages flange 76 of firing rod 75 and flag 94 of drive mechanism 95 of the articulation assembly engages flange or bossed end 78 of articulation rod 79. Actuation of the motor 96 effects linear motion of the flag 94 which moves the articulation rod 79 linearly (axially). The articulation rod 79 is either directly coupled to the joint 54, or coupled to another member or multiple members which are coupled to the joint 54. When moved linearly, the articulation rod 79 effects movement of the jaws 52a, 52b of the stapler 10 to angular positions with respect to the longitudinal axis of the stapler. Note the articulation drive assembly operates in a similar manner as the firing drive assembly of power pack 35 in that when the power pack 90 is secured to the tube 79 by the second output flag 94, linear motion generated at the second output flag 94 is transferred to linear motion of the tube 79. Note that the joint 54 could be configured to provide movement about multiple axis, e.g., two or three axes, and could even be configured to provide unconstrained movement.

Actuation of the motor 83 effects linear motion of the flag of drive mechanism 80 which moves the firing rod 46 linearly (axially). The firing rod either extends through the elongated portion 51 of the loading unit 50 for engagement of the firing mechanism in the jaw 52a or is coupled to another elongated component(s) extending through the elongated portion 51 to engage the firing mechanism in the jaw 52a. Note that the articulation rod or tube 79 can be configured to receive the firing rod so that the firing rod 46 can move within the tube 79 to effect firing and the articulation rod 79 can slide linearly over the firing rod to effect articulation.

After use, the cover can be opened and the power pack 90 removed and charged while the handle assembly 17 (and stapler 10) is sterilized or disposed of if the stapler is a disposable instrument. The power pack 90, like power pack 35 described above, may be reused without requiring sterilization by being inserted into the receptacle of the now-sterilized handle assembly or a different sterile handle assembly. Thus, the removable power pack 90, like power pack 35, does not need to be subjected to the sterilization process and, therefore, contact between the harsh temperatures and/or chemicals of the sterilization process is advantageously avoided.

One or more seals can be utilized for sealing power pack 35 and power pack 90 within the handle assembly 17 so that the power pack remains sterile and is not exposed to bodily fluids during surgical procedures. For example, as discussed above, in the stapler of FIG. 2B, a top seal is positioned at the interface between the cover 27a and the housing 29 of the handle assembly where the cover 27a closes for sealing the opening into the receptacle 27b and, therefore, power pack 35 or 90 from the environment when positioned therein. Further seals can be provided to further seal the receptacle and thus the power pack such as an O-ring placed around the articulation rod 79 to seal the space around the rod 79 and a flexible trigger seal surrounding the lever of the actuator 24' for sealing the internal components of the handle assembly throughout the range of positions of the movable lever 24'. Additional seals can be provided to prevent flow of body fluid through the elongated member 51 and endoscopic portion 16.

As noted above, the power pack 90 can be used with the other staplers disclosed herein, e.g. circular staplers, linear staplers, as well as other instruments wherein two powered functions are desired. The first motor assembly can effect linear motion of a first elongated member to effect a first function of the stapler, e.g., clamping, articulation, firing, and the second motor assembly can effect linear motion of a second elongated member to effect a second different function of the stapler, e.g., clamping, articulation, firing. In the embodiment of FIG. 9D, one function is articulation and another function is staple firing. Note the power pack 90 can also be used with surgical instruments other than surgical staplers such as those illustrated in FIGS. 16 and 17A-17F.

Figure 16:
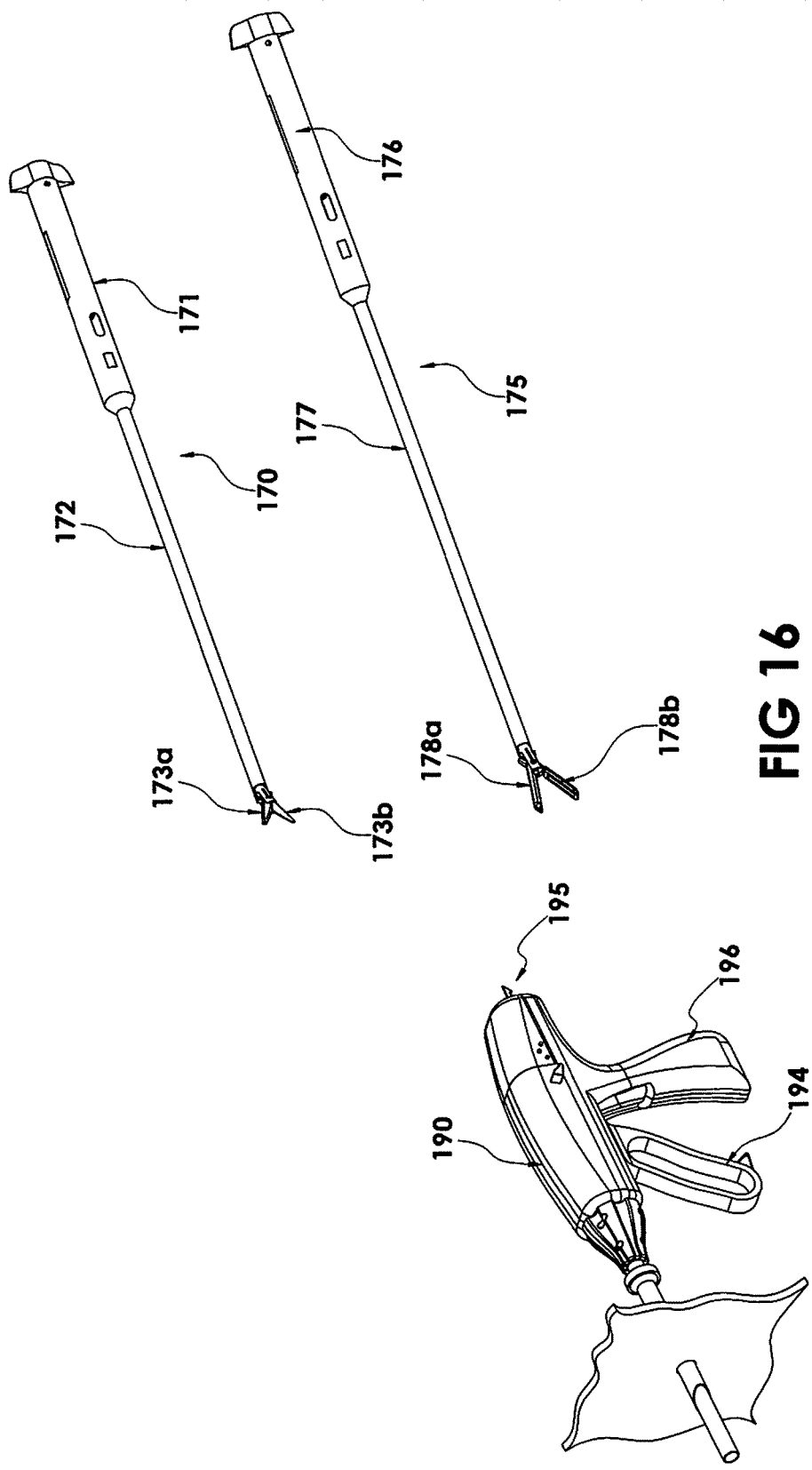
FIG. 16 is a perspective view showing one embodiment of a kit of the present disclosure having two loading units containing different jaw assemblies.

The proximally loaded loading units of the present disclosure can include various end effectors to achieve various functions. They can be offered in a kit containing two or more differently functioning loading units, i.e., differently functioning jaws. FIG. 16 provides one example of a kit having two loading units: Loading unit 170 has a pair of scissors and loading unit 175 has a pair of graspers. More specifically, loading unit 170 has a handle portion 171, an elongated portion 172 and jaws 173a, 173b which are connected to a clamping member extending through elongated portion 172. Movement of the clamping member (clamping rod) within the elongated portion 172 moves the jaws 173a, 173b between open and closed positions to cut tissue between the jaws 173a, 173b. Loading unit 175 has a handle portion 176, an elongated portion 177 and jaws 178a, 178b which are connected to a clamping member extending through elongated portion 177. Movement of the clamping member (clamping rod) within the elongated portion 177 moves the jaws 178a, 178b between open and closed positions to grasp tissue between the jaws 178a, 178b. The jaws 178a, 178b can have grasping surfaces that can include teeth, roughened surfaces, ribs, etc.

Figure 17C:
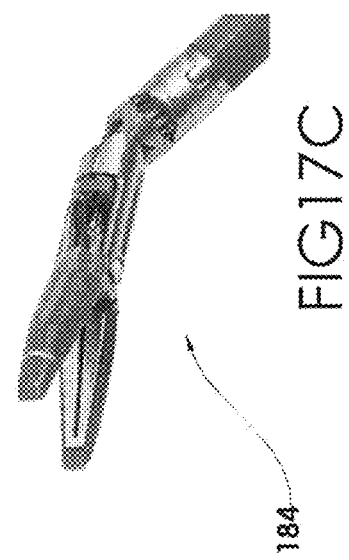
FIGS. 17A, 17B, 17C, 17D, and 17E are perspective views of various jaw assemblies of the loading units of the present disclosure.
Figure 17F:
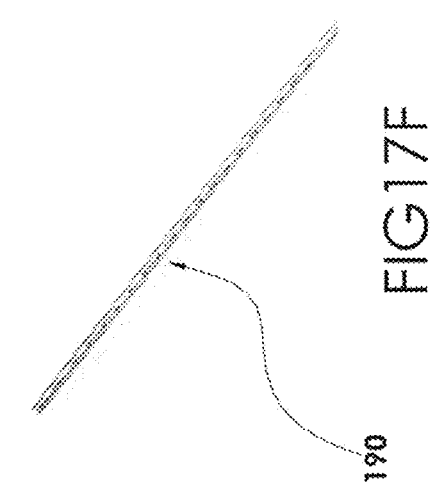
FIG. 17F is a perspective view of a distal end of a loading unit having a tracker for applying tacks to tissue.
Figure 17B:
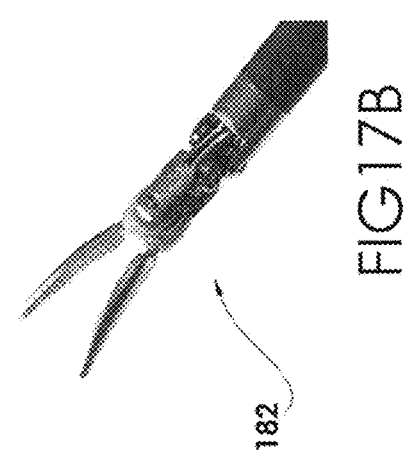
Figure 17E:
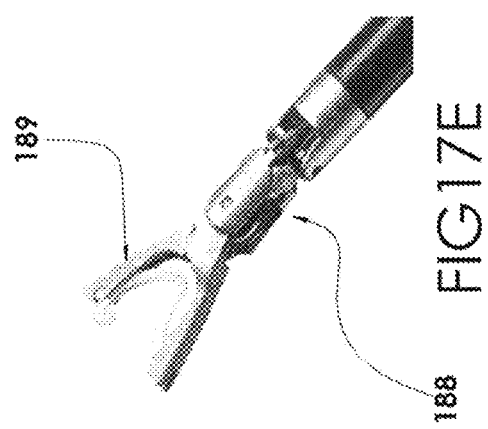
Figure 17A:
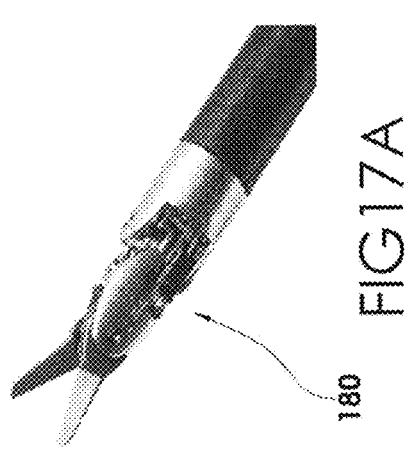
Figure 17D:

The loading units 170 and 175 are insertable and removable through a proximal opening 195 in the instrument 190 (as in proximal openings 23 and 29a described above) while the instrument remains in the body. The instrument 190 can be manually actuated, i.e., by squeezing handle 194 towards handle 196, to effect clamping of the jaws of the loaded loading unit when inserted into the instrument 190, as handle 192 operatively engages the clamping member to effect its linear movement. This engagement can be via a rack and pawl as in FIG. 15. Alternatively, the instrument 190 can be powered by a power pack loaded into the compartment of the stapler in the same manner as power pack 30 or 35 described below, with the proximal opening within the compartment. The power pack drive mechanisms, e.g., an output flag or yoke like flag 42, would extend through the slot in handle portions 171, 176 to engage the clamping member within the loading unit to effect movement of the jaws toward each other. Either one of the jaws can be movable, i.e., pivotable, or both jaws can be movable (pivotable) toward and away from each other, for movement between closed and open positions It should be appreciated that FIG. 16 is just one example of a kit as kits with other combinations of loading units, (and any number of loading units) including loading units containing fasteners, can be provided which are proximally loaded into the instrument in the same manner as loading unit 50 so that various loading units, or loading units that are reloaded with fasteners, can be removed and reinserted while the instrument remains in situ. Alternate jaw assemblies of the proximally loaded loading units are shown in FIGS. 17C-17F by way of example, it being understood that other jaw assemblies could be provided. Jaw assembly 180 provides shears for dissecting tissue, jaw assembly 182 provides graspers to grasp tissue, and jaw assembly 184 is a bipolar dissector to provide electrosurgical energy to tissue grasped between the jaws. In FIG. 17D, instead of jaws, a hook 186 for monopolar cautery extends from the elongated member of the proximally loaded loading unit. In FIG. 17E, the jaws 188 crimp a surgical clip 189 about tissue. In FIG. 17F, the proximally loaded loading unit has an advancer within the elongated member to apply surgical tacks to tissue.

It should be appreciated that the aforedescribed variations of the power packs can also be used with the surgical instruments of FIGS. 16-17F so one or more functions can be powered by the motor. Alternatively, the instruments of FIGS. 16-17F can be manually powered.

Figure 6D:
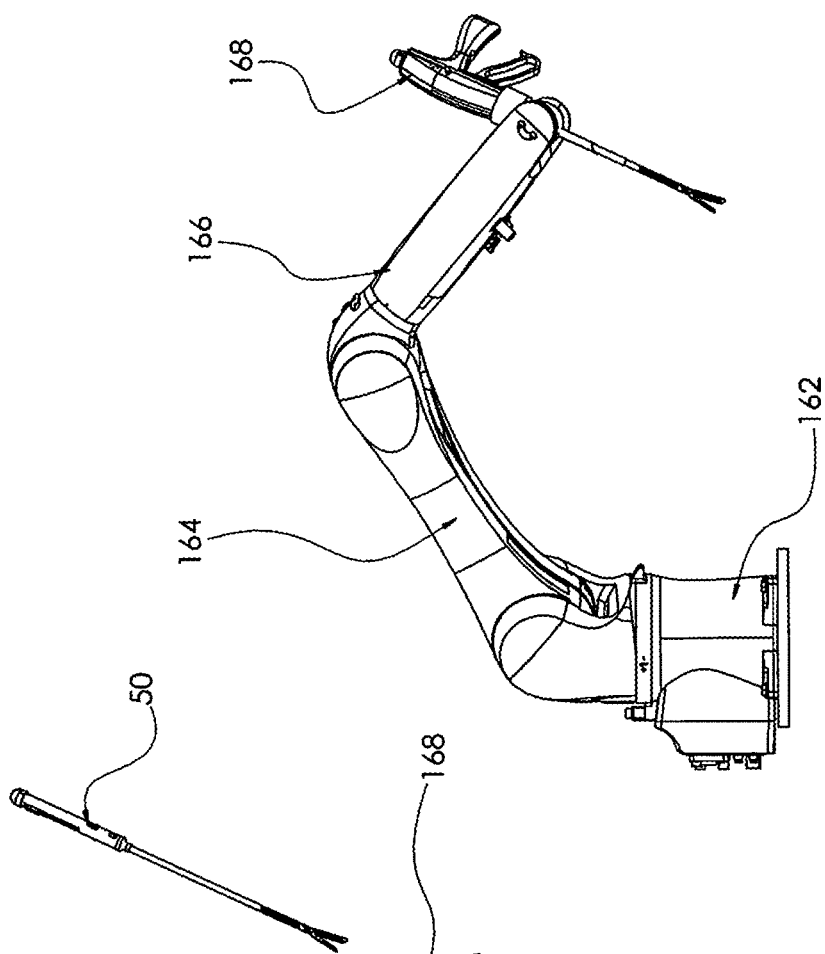
FIG. 6D is a perspective view similar to FIG. 6C showing the loading unit positioned within the stapler.
Figure 6C:
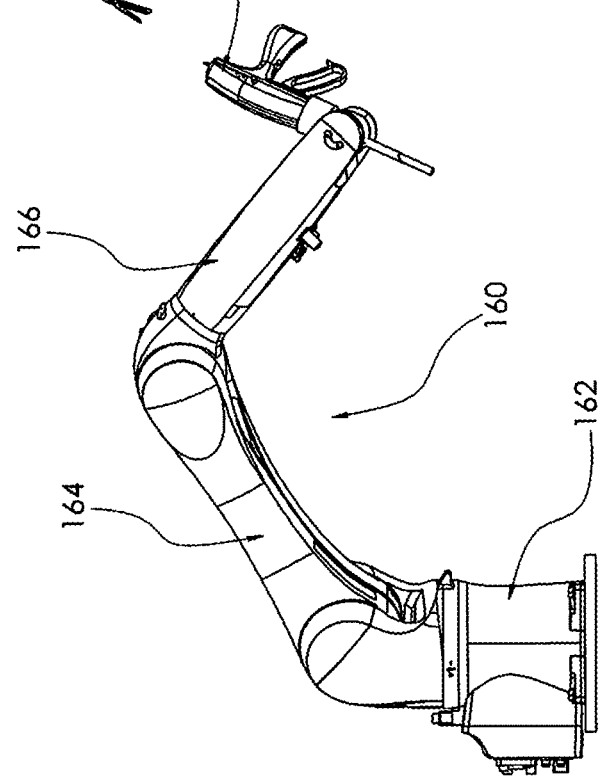
FIG. 6C is a perspective view showing the surgical stapler connected to a robotic arm and the loading unit shown prior to insertion into the stapler.

The power packs disclosed herein can be used in surgery where the clinician manually clamps the jaws and actuates the motor or motors to provide powered staple firing and/or powered jaw articulation or other functions. It is also contemplated that the power packs 30, 35 and 90 can be used with automated robotic driven surgical staplers wherein clamping, motor actuation and any other functions of the instrument are performed robotically, including remote robotic control. This is shown for example in FIGS. 6C and 6D. Robotic arm 160 has a base 162 that is rotatable 360 degrees, an arm 164 connected to the base which moves in a clockwise or counterclockwise direction, and an arm 166 extending from arm 164 which swivels in a motion simulating a person's wrist to provide various degrees of freedom to manipulate the stapler. In FIG. 6C, the stapler is shown held in arm 164 of robotic arm 160 prior to proximal loading of the loading unit 50 (or other loading units described herein) into the stapler 168 (which can be identical to stapler 10 or other staplers disclosed herein). FIG. 6D illustrates the stapler 168 after the loading unit 50 (or other loading units described herein) are proximally loaded into the stapler 168. The degrees of freedom of the arms and base described herein are one example of the robotic arm design that can be utilized as other movements for the base and arms are also contemplated. The robotic arm can also be utilized for the other instruments disclosed herein, e.g., circular staplers, scissors, graspers, etc.

Thus, whether robotically positioned or manually positioned by the user, the present disclosure provides a method for reloading a surgical fastener applier wherein the surgical fastener applier is maintained in a body, e.g., body cavity of a patient, while a) a first loading unit is proximally withdrawn through a proximal opening in the surgical fastener applier and b) a second loading unit is inserted in a distal direction through the proximal opening in the surgical fastener applier. The loading units each have an elongated member, first and second jaws at a distal portion of the elongated member and a firing mechanism movable within the elongated member from a first position to effect firing of fasteners into the tissue clamped between the first and second jaws. The loading units can alternatively have other jaws, e.g., graspers, scissors, etc. for effecting different surgical functions.

In some embodiments, elements such as the rotational member and handle actuator may be omitted and a controller may be configured to generate signals or commands to be received by the surgical stapler in order to actuate the jaws, rotate the tubular shaft or perform other functions. Such a controller may be part of the surgical stapler device or located remotely.

The handle assembly and/or motor assembly may be in wired or wireless communication with an external controller that includes inputs for controlling the surgical stapler Although the apparatus and methods of the subject disclosure have been described with respect to preferred embodiments, those skilled in the art will readily appreciate that changes and modifications may be made thereto without departing from the spirit and scope of the present disclosure as defined by the appended claims.

What is claimed is:

1. A method for reloading a surgical fastener applier comprising the steps of:
    a) with the surgical fastener applier maintained in a body of a patient, withdrawing a first loading unit in a proximal direction through a proximal opening in the surgical fastener applier, the loading unit having an elongated member, first and second jaws at a distal portion and a firing mechanism movable within the elongated member to effect firing of fasteners into the tissue clamped between the first and second jaws; and
    b) with the surgical fastener applier maintained in the body of the patient, inserting a second loading unit in a distal direction through the proximal opening in the surgical fastener applier, the second loading unit having an elongated member, first and second jaws at a distal portion and a firing mechanism movable within the elongated member to effect firing of fasteners into the tissue clamped between the first and second jaws;
    c) wherein the firing mechanism is powered by a motor, the motor contained in a power pack removably mounted in a sealable compartment of the surgical fastener applier, the power pack having a housing containing the motor and a battery
    d) wherein the second loading unit operatively connects to a first actuator within the surgical fastener applier for firing the fasteners and includes an articulation mechanism and the articulation mechanism is engageable with a second actuator within the surgical fastener applier;
    e) wherein the second actuator is powered by a second motor, the second motor contained in the power pack removably mounted in the surgical fastener applier.

2. The method of claim 1, wherein the power pack includes an engagement member, the engagement member removably engageable with the articulation mechanism in the loading unit to effect articulation of the first and second jaws from a linear position to a position angled with respect to a longitudinal axis of the elongated member when the power pack is loaded into the compartment.

3. The method of claim 1, wherein the second loading unit has a different structure than the first loading unit removed from the surgical fastener applier.

4. The method of claim 1, wherein the loading unit has an engagement structure engageable with a side wall of a housing of the surgical faster applier to retain the loading unit.

5. The method of claim 1, wherein the elongated member of the second loading unit has an elongated slot to receive an engagement member of the power pack for engagement of a drive mechanism of the power pack with the firing mechanism of the second loading unit.

6. The method of claim 1, wherein a housing of the surgical faster applier has a lumen extending longitudinally distally from the proximal opening and the second loading unit is insertable through the lumen in the housing.

7. The method of claim 1, wherein the first loading unit includes a cartridge containing the fasteners, the method includes removing the cartridge from the first loading unit after firing and replacing with another cartridge having fasteners.

* * * * *